(12) United States Patent
Michels

(10) Patent No.: US 7,354,718 B2
(45) Date of Patent: Apr. 8, 2008

(54) MOLECULAR DISSECTION METHOD USING TRANS-SPLICING TO DESIGNED SPLICED LEADER SEQUENCES, GENES, AND CONSTRUCTS THEREOF

(76) Inventor: William John Michels, 2227 Roosevelt Ave., #1, Berkeley, CA (US) 94703

( * ) Notice: Subject to any disclaimer, the term of this patent is extended or adjusted under 35 U.S.C. 154(b) by 0 days.

(21) Appl. No.: 11/027,224

(22) Filed: Dec. 30, 2004

(65) Prior Publication Data
US 2005/0186597 A1    Aug. 25, 2005

Related U.S. Application Data

(60) Provisional application No. 60/558,634, filed on Apr. 1, 2004, provisional application No. 60/533,273, filed on Dec. 31, 2003.

(51) Int. Cl.
*C12Q 1/68*    (2006.01)
(52) U.S. Cl. .......................................... 435/6; 435/91.3

(58) Field of Classification Search ..................... None
See application file for complete search history.

(56) References Cited

U.S. PATENT DOCUMENTS

2004/0220127 A1    11/2004    Sternberg et al.

OTHER PUBLICATIONS

Goldring et al., Experimental Parasitology, vol. 84, 1996, pp. 28-41.*
Colosimo and Sengupta, Specification of Individual Olfactory Neuron Function, Abstract 124, West Coast Worm Meeting 2002.

* cited by examiner

*Primary Examiner*—James S Ketter

(57) ABSTRACT

The presently disclosed subject matter generally relates to a method for detectably labeling ribonucleic acid molecules expressed in cells of interest. Also provided are methods for isolating ribonucleic acid molecules derived from genes that are expressed in cells of interest.

23 Claims, 3 Drawing Sheets

A. Point Mutations

B. Insert nucleotides to 5' end of SL

C. Insert nucleotides to 3' end of SL

D. Insert nucleotides internally

A. SL1 RNA expression (black).

B. Animals transformed with U2-3::Tagon (Tagon expression = dark grey).

C. Animals transformed with vit-2/6::Tagon (Tagon expression = dark grey)

D. Animals transformed with mec-3::Tagon (Tagon expression = dark grey)

MOLECULAR DISSECTION METHOD USING TRANS-SPLICING TO DESIGNED SPLICED LEADER SEQUENCES, GENES, AND CONSTRUCTS THEREOF

CROSS REFERENCE TO RELATED APPLICATIONS

This application is based on and claims priority to U.S. Provisional Application Ser. No. 60/533,273, filed Dec. 31, 2003, and U.S. Provisional Application Ser. No. 60/558,634, filed Apr. 1, 2004, the disclosure of each of which is incorporated herein by reference in its entirety.

FIELD OF INVENTION

The presently disclosed subject matter generally relates to a method for detectably labeling ribonucleic acid molecules expressed in cells of interest. Also provided are methods for isolating ribonucleic acid molecules derived from genes that are expressed in cells of interest.

| Table of Abbreviations | |
|---|---|
| 5'UTR | 5'-untranslated region |
| cDNA | complementary DNA |
| CMV | cytomegalovirus |
| DHFR | dihydrofolate reductase |
| DNA | deoxyribonucleic acid |
| dsRNA | double stranded ribonucleic acid |
| DTPA | diethylenetriamine pentaacetic acid |
| EDTA | ethylenediamine tetraacetic acid |
| EGTA | ethyleneglycol tetraacetic acid |
| FACS | Fluorescence Activated Cell Sorting |
| FRET | fluorescence resonance energy transfer |
| G418 | an aminoglycoside antibiotic |
| GFP | green fluorescent protein |
| HPRT | hypoxanthine phosphoribosyl transferase |
| hsp | heat shock protein |
| HSV-tk | herpes simplex virus thymidine kinase |
| IRES | internal ribosome entry site |
| LCM | Laser Capture Microdissection |
| MAR | matrix attachment region |
| miRNAs | micro ribonucleic acids |
| ORF | open reading frame |
| PAB | poly-A binding protein |
| PCR | polymerase chain reaction |
| PGK | phosphoglycerate kinase |
| PSE | Proximal Sequence Element |
| RACE | Rapid Amplification of cDNA Ends |
| RDA | representational difference analysis |
| RNA | ribonucleic acid |
| RNAi | RNA interference |
| SAGE | serial analysis of gene expression |
| SAR | scaffold attachment region |
| SDS | sodium dodecyl sulfate |
| SL | spliced leader [mini-exon] |
| SLRNA | spliced leader RNA gene |
| SSC | standard saline citrate |
| SSH | suppression subtraction hybridization |
| SV40 | simian virus 40 |
| TAFs | Transcription Associated Factors |
| $T_m$ | thermal melting point |
| UTR | un-translated region |
| XIST | X chromosome inactivation transcript |

BACKGROUND

Advances in understanding multicellular organisms are encumbered because of inherent problems with cell and/or tissue heterogeneity. Particularly challenging, with regard to studies of cell type and/or tissue-specific gene expression, is the fact that cells and tissues of interest often cannot be isolated away from unwanted cells and tissues (White, Dunning et al. 1993)(Halgren, Fielden et al. 2001). Lay persons may observe that tissues and organs contain multiple different cell types not easily examined in isolation; for example, meat contains predominantly muscle but also contains interspersed nerves, connective tissue, tendon, blood, blood vessels, and fat. This heterogeneity is easily visible at the macroscopic level.

Microscopic examples of cellular heterogeneity include 1) nervous tissue, where in the presence of interspersed supporting cells such as glia, multiple different neuronal types interconnect to form a nervous system, and 2) skin, where each of the three layers contain multiple different cell types such as a) melanocytes and keratinocytes in the epidermal layer, b) macrophages, fibroblasts, and lymphocytes in the dermal layer, and c) endothelial cells and neurons in the hypodermal layer. Isolation or examination of individual cell types in heterogeneous tissue, and/or elucidating or 'profiling' expressed gene sequences from individual cell types, is presently difficult.

The inability to precisely isolate cell types and/or profile their molecular (i.e. nucleic acid) constituents from heterogeneous tissue can lead to incorrect assignment of gene expression, misinterpretation of gene function, and misinterpretation of functional elements controlling gene expression. This difficulty encumbers understanding multicellular organisms despite the availability of extensive genomic DNA sequence data, such as data obtained via the Human Genome Project.

A serious consequence of this 'isolation' or 'profiling' problem is the inability to isolate and compare differentially expressed genes within a heterogeneous tissue, that is, genes that are expressed at different levels, or not at all, between any two different cell-types within the tissue of interest. This difficulty encumbers identification of gene candidates in cells, tissues, organs, and whole organisms responsible or implicated in functions such as tissue growth, development, cell fate specification, cell death, organogenesis, and in aging. The problem exists in both normal and disease states. This difficulty encumbers development of reasonable hypotheses and the testing of precise molecular mechanisms in normal and diseased tissue, since putative genes thought to be involved are often unknown and/or poorly localized by standard methods.

A second serious consequence of this 'isolation' or 'profiling' problem is the inability to accurately compare levels of gene expression between tissues of varying complexity in an organism, that is, different tissues that contain widely different numbers of cell types. For example, if a gene appears to be expressed at a 'high' level in a simpler tissue such as liver, containing few putative cell types, as compared to a complex tissue such as brain tissue containing tens, hundreds, or possibly thousands of cell types, the comparison is virtually meaningless. One could postulate that a cell type present in complex (e.g. brain) tissue at a scant frequency expresses the same gene at a level equal to or many-fold greater than in the simpler (e.g. liver) tissue. This difficulty encumbers understanding environmental sensitivity to chemical compounds, and encumbers the appropriate choice of cellular targets for therapeutic intervention, for example, to reduce unwanted side effects.

A third serious consequence of this 'isolation' or 'profiling' problem is that it is presently difficult to determine if two cells express identical or near identical sets of genes, as would be expected for a given cell type. Because of the difficulty in determining which and how many cells belong to a particular cell type class by present empirical methods, two further difficulties arise: 1) it is difficult to accurately measure and express the similarity (or dissimilarity) of any two cell types in complex tissue, organs, or whole organisms, and 2) it is difficult to determine or estimate an absolute number of different cell types within complex tissue, organs, or whole organisms.

Cell types are commonly categorized on the basis of morphology, and/or cell surface antigens, and/or promoter activation. These empirical measures arguably fail to give a definitive answer as to whether or not the category of 'positive' cells actually constitute an individual cell type, since these measures often rely on the expression of a limited set of gene products, even as few as one gene product (e.g. a cell surface antigen).

A rigorous measure of whether two similar cells in a complex tissue actually constitute a single cell type would be a comparison of the sets of genes expressed in each cell. Different cells expressing identical and/or near identical sets of genes (e.g. represented as overlapping sets in a Venn diagram) can be thought of as constituting a single cell type. For complex solid tissue, rigorous measures for defining cell types, the number of cell types, and the relative similarity between different cell types would be highly desirable.

As an example, the nematode *Caenorhabditis elegans* has a nervous system as an adult animal of 302 neurons. These neurons have been categorized into 118 different cell types on morphological grounds (White 1986). It is presently unknown if these putative 118 cell types are simply cells that bear a superficial morphological resemblance to each other but are otherwise distinct. Two possibilities exist: in reality the number of cell types—as classified by cells expressing identical sets of genes—is actually much lower, possibly as few as a dozen different neuronal types. Alternatively as many as 302 different neuronal cell types may be present in *C. elegans*, that is, all neuronal cells are unique as defined by the criteria of expressed gene sets. This question can be extended to other complex tissues and/or organs in multicellular organisms, such as brain tissue, spinal cord, cardiac tissue, liver, kidney, etc.

The question of cell type number can even be extended to tissues that appear to be superficially simple, or to contain identical cells. For example, developing *Drosophila* embryos contain superficially identical cells at the cellular blastoderm stage. However, despite their superficial similarity, cells are already expressing genes involved in determining body plan in intricate and precise banding patterns. In *Drosophila*, these patterns are generated according to anterior-posterior and dorsal-ventral position. These data demonstrate mere morphological similarity between cells is no guarantee that they are expressing identical sets of genes. In fact, superficially similar cells may be responding to distal inductive signals.

The inability to easily assign cells to cell types, to determine a number of different cell types for a given tissue, and to accurately measure and express the similarity between different cell types within a specific tissue encumbers a) understanding and elucidating cellular roles in normal and diseased tissue during growth, development, and aging, b) understanding and elucidating environmental toxicology, c) appropriate choice of cellular targets for therapeutic intervention, and d) appropriate choice of cellular methods and reagents for therapeutic intervention (e.g. cell-based and/or tissue-based therapy).

For example, introduction of exogenous cells and or tissues (the basic technique adapted for use in therapy involving stem cells) would be critically and materially advanced as a therapeutic technique if exogenously-added cells and/or tissues could be reliably determined to be—or could be predictably induced to become—identical, similar, and/or compatible with endogenous cells and/or tissues.

The most common approach to cellular isolation in solid tissue is microdissection. Unfortunately, microdissection is often a difficult and error-prone technique. Microdissection also potentially allows for the disruption of normal gene expression patterns by the mechanical acts of cutting, crushing, and/or scraping, and its use may not result in data that accurately reflect in vivo gene expression patterns and levels. Thus novel isolation and/or profiling technique(s) are required precisely where microdissection is technically difficult or impossible, or may cause unforeseen changes in gene expression.

Cellular heterogeneity is a problem particularly evident in solid, complex tissues of the human body such as the brain, spinal cord, kidney, and in endocrine tissues such as the pituitary gland and pancreatic islet cells, etc. (Takeda, Yano et al. 1993; Chabardes-Garonne, Mejean et al. 2003; Kaestner, Lee et al. 2003; Cras-Meneur, Inoue et al. 2004), but is also relevant to solid tumors of the human body (Amatschek, Koenig et al. 2004), as well as in cells and tissues of model vertebrate organisms. Additionally, this problem is present in invertebrates and lower metazoans of biomedical, agricultural, and/or environmental interest, such as pathogenic and non-pathogenic nematodes, where a tissue or organ can consist of as few as tens or hundreds of cells (Andrews, Bouffard et al. 2000). As a consequence, the reliability and usefulness of modern techniques such as the use of DNA microarrays and serial analysis of gene expression (SAGE) is sharply limited.

Presently, the post-genomic era of biotechnology has made an organism's entire DNA sequence available to the biotechnology researcher, often on a chip. The implication for studying many model organisms is clear: gene function can be predicted by analogy to known genes, clones of genes are available, computer programs can rapidly predict locus elements such as promoters, enhancers, and splice sites, and genes and gene sequences can be compared to reference genomes or model organisms, etc.

Despite these advances, the era of post-genomic research has barely begun. Novel methodologies are required to advance an understanding of organisms, just as DNA sequencing advanced an understanding of genomes. Studies of complex interactions between cells in tissues, organs, and organisms promise to reveal a fascinating array of control mechanisms in the field of 'tissue dynamics.' Mechanisms include autocrine, paracrine, and endocrine control. The functional interplay of genes in different cell types will most likely be deciphered in well-studied model organisms. However the genomes of many organisms, including well-studied model organisms, remain un-interpretable despite the expenditure of resources to decipher their genetic content (e.g., cloning, mapping, and sequencing). This is because patterns of gene expression in complex tissue remain poorly understood. This experimental difficulty is present in both well-studied and recently introduced model organisms. For example, sequencing of the genome of the tunicate *Ciona intestinalis* has recently been completed, but the usefulness of this genomic information is limited because of insufficient knowledge of tissue-specific gene expression. Thus a great need exists for novel cell type-specific analytical techniques in advancing an understanding of the functional interplay between genes in most, if not all, metazoan organisms.

Currently, researchers often know an organism's genomic resources (e.g. genes), but not where and when the genes are expressed (i.e., in which tissues). Techniques are available that can be used to determine the expression pattern of individual genes (e.g., in situ hybridization), but this process is time-consuming and error-prone for the analysis of thousands, or tens of thousands, of genes. Furthermore, this analysis becomes even more burdensome when one considers that gene expression patterns are desired not only from normal tissues, but also from tissues subjected to various factors such as mutation, transformation, infection, and/or chemical (e.g., pharmacological) treatment.

For example, brain tissue contains a poorly understood cell type known as astrocytes, implicated in response to environmental insult (Sturrock 1988). Determining astrocyte-specific gene expression presents an enormous challenge, even in those organisms for which large amounts of brain tissue are readily available. Individual cell types are usually determined by histochemical and/or morphological methods. Cell type-specificity of individual genes, such as astrocyte-specific gene expression, is determined by serial techniques including in situ hybridization of the gene of interest and/or antibody detection of the gene product. For tissues that contain multiple different cell types (estimated tens to hundreds), it is presently difficult to isolate, examine, and/or profile the estimated hundreds or thousands of genes expressed in any particular cell type.

The actual physical isolation of specific cell types serves at least two different goals. The first is for the analysis of genetic material (DNA and RNA) from these cells, which is generally referred to as "molecular" analysis, that is, relating to molecular biology. The second is to examine cell growth in culture (cell culture) to investigate cellular responses, media requirements, autonomous/non-autonomous development, and expressed genes responsible for these characteristics. Once isolated, comparing gene expression in any two tissues of an organism is a valuable technique for determining gene function.

Paradoxically, it is presently easier to study the differential expression of genes in a mouse, a frog, or a human being than in some classically studied animals such as flies and worms, the latter of which are related to parasitic animals that ravage the human population. Thus, a rapid method for elucidating (i.e. profiling) differential patterns of gene expression, otherwise known as a "molecular dissection" method, with or without cellular isolation, would be of great utility for the millions of species of poorly understood metazoan organisms.

Many of these poorly-understood metazoan organisms have profound biomedical, agricultural, and environmental relevance. For example, the World Health Organization estimates that two billion people worldwide—one-third of the world's population—are infected with worms such as *Schistosoma* and soil-transmitted helminths (STH). Two hundred million people are infected with *Onchocerca volvulus*, the cause of river blindness. Lymphatic filariasis and elephantiasis, which affect 120 million people worldwide, are caused by the related nematodes *Brugia malayi* and *Wucheria bancrofti*.

Organisms of agricultural importance include the nematode *Heterorhabdis bacteriophora*, which is commercially available as a biocontrol agent (Riddle, Blumenthal et al. 1997). *H. bacteriophora* promiscuously parasitizes insect larvae. *Haemonchus contortus*, an intestinal parasite of sheep, is a serious agricultural pathogen. Non-pathogenic nematodes and related species have been proposed as organisms with potential for environmental toxicity testing and bioremediation (Williams and Dusenbery 1990; Donkin and Dusenbery 1993; Cressman and Williams 1997; Custodia, Won et al. 2001).

Developing new techniques for investigating tissue-specific gene expression is important for understanding multicellular organisms. Knowledge gained will allow gene pathways to be defined more rapidly, and will allow pharmacological targets to be selected with greater precision. Potential commercial products include, but are not limited to tissue-specific microarrays from model and parasitic organisms, cDNA libraries from specific cells and cell types, host determinant genes for pathogenic species, pharyngeal pumping genes for pharmacologic intervention, tissue-specific detoxifying genes induced in model and parasitic organism, and services to determine promoter activity in these metazoans. Ultimately these commercial tools will contribute to alleviating human suffering, increasing agricultural production, and improving the environment.

An important observation is that many of these poorly understood metazoan organisms of biomedical, agricultural, and environmental importance utilize an endogenous trans-splicing reaction in normal RNA processing. Other organisms may be induced to perform this trans-splicing reaction if no known reaction already exist. Thus cell isolation and/or cell-profiling techniques based on novel and inventive utilization of this reaction would have beneficial biomedical, agricultural, and environmental effects.

Thus, improved methods for use in identifying differential gene expression in cells and tissues that are not amenable to isolation represent a long-felt and ongoing need in the art. This and other needs are addressed by the presently disclosed subject matter.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to some embodiments of the presently disclosed subject matter, whether listed in this Summary or not. To avoid excessive repetition, this Summary does not list or suggest all possible combinations of such features.

The presently disclosed subject matter provides a method for isolating a trans-spliced ribonucleic acid molecule from a cell. In some embodiments, the method comprises (a) introducing into the cell a nucleic acid molecule encoding a derivatized spliced leader RNA (SLRNA) molecule, wherein the derivatized SLRNA molecule comprises a spliced leader sequence comprising a unique sequence; (b) expressing the derivatized SLRNA in the cell, wherein the expressing results in the spliced leader sequence being trans-spliced onto a ribonucleic acid molecule; and (c) isolating the trans-spliced ribonucleic acid molecule comprising the spliced leader sequence. In some embodiments, the method further comprises sequencing the trans-spliced ribonucleic acid molecule or a reverse transcription product thereof.

The presently disclosed subject matter also provides a method for identifying a plurality of ribonucleic acid molecules expressed in a cell. In some embodiments, the method comprises (a) introducing into the cell a derivatized spliced leader RNA (SLRNA) molecule, wherein the derivatized SLRNA molecule comprises a spliced leader sequence comprising a unique sequence; (b) expressing the derivatized SLRNA in the cell, wherein the expressing results in the spliced leader sequence being trans-spliced onto a ribonucleic acid molecule; and (c) isolating the trans-spliced ribonucleic acid molecule comprising the spliced leader sequence. In some embodiments, the method further comprises sequencing at least one of the plurality of trans-spliced ribonucleic acid molecules or a reverse transcription product thereof. In some embodiments, the method further comprises creating a library comprising the plurality of trans-spliced ribonucleic acid molecules. In some embodiments, the method further comprises sorting and/or arraying trans-spliced ribonucleic acid molecules or reverse transcription and/or library products thereof.

The methods of the presently disclosed subject matter can be performed on or in any cell. In some embodiments, the cell is present in an organism. In some embodiments, the organism is selected from the group consisting of cnidarians, ascidians, nematodes, trematodes, cestodes, helminthes, avians, and mammals. In some embodiments, the organism is selected from the group consisting of *C. elegans, Schistosoma* sp., soil-transmitted helminthes, *Onchocerca volvulus, Brugia malayi, Heterorhabditis bacteriophora, Haemonchus contortus*, and *Wucheria bancrofti*.

In some embodiments of the presently disclosed subject matter, a nucleic acid molecule is introduced into the cell. In some embodiments, the introducing is accomplished by introducing into the cell a nucleic acid encoding a transgenic SLRNA molecule, wherein the transgenic SLRNA molecule comprises a spliced leader sequence comprising a unique sequence. In some embodiments, the methods further comprise mutagenizing an endogenous SLRNA gene to a non-functional form.

The presently disclosed subject matter also provides a method for detectably labeling a ribonucleic acid derived from a gene expressed in a cell of interest. In some embodiments, the method comprises introducing into the cell a nucleic acid molecule encoding a 5' spliced leader (SL) sequence, wherein the 5' SL sequence comprises a detectable label. In some embodiments, the nucleic acid molecule comprises a 5' spliced leader (SL) sequence operatively linked to a promoter capable of directing transcription of the 5' SL sequence in the cell of interest. In some embodiments, the cell of interest is present in an organism. In some embodiments, the organism is selected from the group consisting of cnidarians, ascidians, nematodes, trematodes, cestodes, helminthes, avians, and mammals. In some embodiments, the organism is selected from the group consisting of *C. elegans, Schistosoma* sp., soil-transmitted helminths, *Onchocerca volvulus, Brugia malayi, Heterorhabditis bacteriophora, Haemonchus contortus*, and *Wucheria bancroffi*.

In some embodiments of the presently disclosed subject matter, the cell of interest is selected from the group consisting of an endothelial cell, a gonadal cell, a gut cell, neuronal cells (including, but not limited to motor neurons, sensory neurons including mechanosensory, thermosensory and chemosensory, interneurons, ring neurons, serotonergic neurons, glutamatergic neurons, GABAergic neurons, dopaminergic neurons, and cholinergic neurons), hypodermal cells, muscle cells, duct cells, sheath cells, pharyngeal cells, vulval cells, ray cells, labial cells, excretory cells, sperm, oocytes, and coelomocytes.

Accordingly, it is an object of the presently disclosed subject matter to provide a new method for examining differential gene expression in a tissue. This object is achieved in whole or in part by the presently disclosed subject matter.

An object of the presently disclosed subject matter having been stated hereinabove, other objects will be evident as the description proceeds and as best described herein below.

BRIEF DESCRIPTION OF THE DRAWINGS

In FIG. 2A, point mutations are introduced into the SL exon. In FIG. 2B, a unique sequence is added to the 5' end of the SL exon. In FIG. 2C, a unique sequence is added to the 3' end of the SL exon. In FIG. 2D, a unique sequence is added to the middle of the SL exon.

FIG. 3A depicts the expression of an endogenous SL1 RNA gene in a wDf1 mutant and a wild type N2 animal. FIG. 3A depicts the expression of a Tagon transgene operably linked to a U2-3 promoter in a wDf1 mutant and a wild type N2 animal. Ubiquitous expression would be expected in each animal due to the activity of the U2-3 promoter in all cells. FIG. 3C depicts the expression of a Tagon transgene operably linked to a vit-2/6 promoter. In the left panel, no expression is expected in N2 animals (i.e. non-transgenic animals). In the right panel, expression along the gut is expected in vit-2/6::Tagon transgenic animals due to the activity of the vit-2/6 promoter in cells of the gut. In FIG. 3D, expression of a Tagon transgene operably linked to a mec-3 promoter is depicted. The left panel depicts a negative (i.e. non-transgenic) control. The middle panel depicts the expression of the Tagon sequences in a transgenic animal comprising a mec-3::Tagon transgene. Expression is depicted only in touch cells. When the mec-3::Tagon transgene is introduced into an animal homozygous for the unc-86 mutation however, the Tagon sequences are not expressed due to the inactivity of the mec-3 promoter in unc-86$^{-/-}$ cells (see right panel).

DETAILED DESCRIPTION

Figure 1:
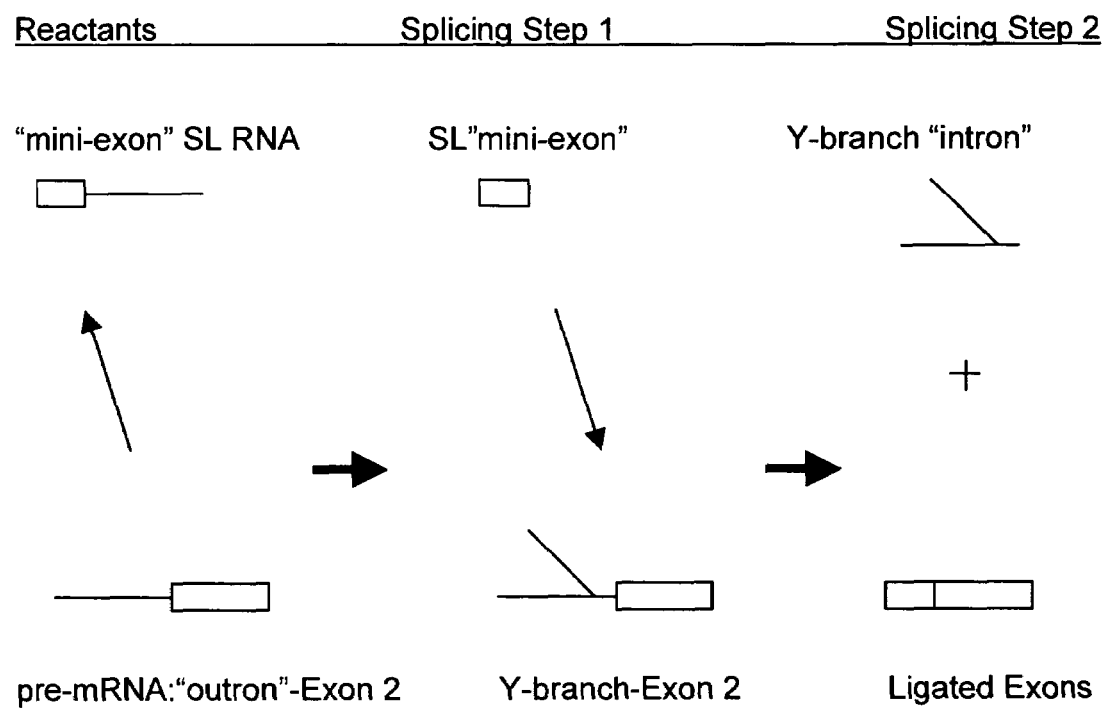
FIG. 1 schematically depicts a representative trans-splicing mechanism. In this reaction, a common "mini-exon" known as the spliced leader (SL) is added to the 5' end of a gene transcript in a reaction analogous to cis-splicing. In the first step, the 2'-hydroxyl group of an internal adenosine in the pre-mRNA attacks at the 5' splice site on the SL RNA, creating a Y-branched intermediate, leaving a 3'-hydroxyl group on the SL mini-exon. In the second step the 3'-hydroxyl group of the SL mini-exon attacks at the 3' splice site on the pre-mRNA, ligating the Spliced Leader to the 5'-end of the mRNA transcript and releasing a Y-branched RNA including the intron and distal SLRNA sequences. Spliceosomal cis- and trans-splicing mechanisms bear resemblance to autocatalytic self-splicing in Group II introns (Sharp 1987; Chin and Pyle 1995; Michels and Pyle 1995).

The present subject matter will be now be described more fully hereinafter with reference to the accompanying Examples, in which representative embodiments of the presently disclosed subject matter are shown. The presently disclosed subject matter can, however, be embodied in different forms and should not be construed as limited to the embodiments set forth herein. Rather, these embodiments are provided so that this disclosure will be thorough and complete, and will fully convey the scope of the presently disclosed subject matter to those skilled in the art.

Throughout the specification and claims, a given chemical formula or name shall encompass all optical and stereoisomers as well as racemic mixtures where such isomers and mixtures exist.

1. General Considerations

A method that would directly allow the comparison of genes expressed in any one cell type (for example, neurons) to genes expressed in any other cell type (for example, glia) present in that tissue, or in other tissues of an organism (for example, heart or kidney), would facilitate a more complete understanding of the role of particular cell types in tissue and/or organ function. For example, the role glia play in normal brain function could be elucidated by using the techniques described herein.

In both simple and complex tissues, genes are induced and/or repressed in a cell-type specific manner in response to infection, mutation, chemical (e.g., pharmacological) treatment, and/or unknown causes (disease states). Changes in a gene's expression in a highly complex tissue, although usually detectable on a molar level, require additional methodologies and techniques to determine the precise cellular site of induction and/or repression, such as in situ hybridization and/or antibody detection. Although cumbersome, this method of determining cell-type specific gene induction and/or repression is in general use.

An improved technique would be to use a novel technique to first isolate genes expressed in specific cell-types from complex tissue. All derived genes will be from the cell type of interest by definition. Experimental conditions could be used to induce differential gene expression. For example, astrocytes, a neuronal cell type, are known to induce genes in response to insult and/or injury. If astrocyte genes can be isolated first, then changes in astrocyte gene expression due to experimental conditions (insult, damage, injury, hypoxia, etc.) can be easily investigated. A method of this sort can thus be used to discover a class of "insult-inducible" genes in astrocytes, and thus elucidate the role astrocytes play in response to brain injury or disease.

Previously, because of difficulties with enzymes used in molecular cloning, the dominant issue in cDNA library production was completeness: that is, assuring that the resultant library included copies of mRNA transcripts expressed in the tissue of interest, no matter how rare. Concerns over cellular heterogeneity and cellular contamination were secondary. As concerns over completeness have diminished over time, the accuracy of cDNA libraries (i.e., assuring that mRNA probes, cDNA libraries, and cDNA microarrays are actually wholly derived from the tissue or cell type of interest) has become a serious concern for biomedical researchers. For example, it is presently difficult to determine global changes in gene expression in neurons of a particular neurotransmitter type in complex neuronal tissue. There are few methods for isolating-genes in a manner that is glutamatergic-neuron specific, GABAergic-neuron specific, dopaminergic-neuron specific, serotonergic-neuron specific, glia-specific, and/or astrocyte-specific. A general method that could efficiently isolate mRNA from these cells for use as a probe in microarray analysis would be a boon for researchers studying neurological disease states.

The methodology described herein is immediately adaptable to various metazoan animals, since they perform an endogenous RNA splicing reaction that can be co-opted by the methods described herein.

Many organisms have been sequenced in their entirety, however, DNA sequencing is only the first step in understanding the biology of an organism. Deciphering tissue-specific gene expression by cDNA or microarray analysis is a necessary step for understanding multicellular organisms. Tissue-specific libraries and microarrays derived thereof are available for the tissues of many organisms. A number of caveats exist in the use of these resources. First, for even tissues of comparatively low complexity (e.g. muscle or liver) there can be no assurance that these libraries are composed of a single cell type. Second, cDNA libraries from complex tissues such as 'brain' or 'kidney' contain multiple cell types by definition, often tens or even hundreds of cell types. In addition to problems of 'accuracy' (i.e. knowing the cell type from which a particular isolated gene is derived), the availability of these libraries is biased towards vertebrate tissues and/or animals. Thus the availability of tissue-specific and/or cell type-specific libraries for other organisms of biomedical, agricultural and/or environmental importance is often quite limited. Finally, microarray analysis using heterogeneous tissues for both probe and target (cDNA microarrays) will likely experience high experimental variability due to cellular heterogeneity per se.

Techniques are available that can determine the expression pattern of individual genes, such as in situ hybridization. However in situ hybridization is an iterative technique analyzing one gene transcript at a time. In situ hybridization is time-consuming and error-prone for the analysis of thousands, or tens of thousands, of genes. A technique known as Laser Capture Microdissection (LCM) is able to isolate individual cells from complex tissues, such as solid tumors for genomic analysis. Because this technique is designed to isolate individual cells, cellular markers such as surface antigens often must be used to classify cell types for the identification, collection, and/or study of a particular cell type. Isolated cells cannot be pooled (or 'binned') without a rigorous analysis of this sort. Also, it is labor-intensive and time-consuming to isolate cells of a particular cell type that are dispersed in an organism. Finally, since the cells of interest must be surface-exposed, this technique cannot be used to isolate many cell types without manual dissection, which often itself causes changes in gene expression.

To circumvent difficulties in microdissection two techniques, "mRNA-tagging" and "GFP/FACS," are methods used in organisms including the model organism *Caenorhabditis elegans* (Reinke 2002). Although these techniques can and have been adapted to other organisms, each technique has its own limitations. The genomic technique of "mRNA-tagging" allows the recovery of poly-$A^+$ mRNAs by introducing a molecular tag into the poly-A binding protein (PAB). This technique might be sensitive to poly-A tail length, possibly explaining why rank order of gene enrichment is more reproducible than absolute level of gene enrichment (Roy, Stuart et al. 2002). The GFP/FACS method is a cellular method whereby cells are labeled with green fluorescent protein (GFP) during normal development, plated, and $GFP^+$ cells are recovered using Fluorescence Activated Cell Sorting (FACS). In this technique, the cell culture isolation required to identify cells can prevent the detection of normal gene expression induced by cell-cell interactions (Zhang, Ma et al. 2002).

New methods of cell type-specific identification and gene isolation represent a class of techniques for which improvements could provide great benefits for researchers. These new methods can allow the researcher to identify and isolate important genes without resorting to more complex, error-prone, and time-consuming procedures such as flow cytometry, micro-dissection, subtractive hybridization, representational difference analysis (RDA), suppression-subtraction hybridization (SSH), etc.

Invertebrate and vertebrate organisms mature nascent RNA transcripts by the process of RNA splicing, mediated by a cellular component called a spliceosome. This process can be subverted by the introduction of exogenous genes that interact with the spliceosome. Manipulating this process allows individual mRNA transcripts to be tagged in a tissue-specific and/or cell type-specific manner as described herein.

Spliced leader (SL) addition trans-splicing is an RNA processing reaction widely utilized in metazoan organisms such as cnidarians, nematodes, and ascidians (Nilsen 2001). In this reaction, a common "mini-exon" known as the spliced leader is added to the 5' ends of many different genes in a reaction analogous to cis-splicing (see FIG. 1). In the first step, the 2'-hydroxyl group of an internal adenosine in the pre-mRNA attacks at the 5' splice site on the SL RNA, creating a Y-branched intermediate, leaving a 3'-hydroxyl group on the SL mini-exon. In the second step the 3'-hydroxyl group of the SL mini-exon attacks at the 3' splice site on the pre-mRNA, ligating the Spliced Leader to the 5'-end of the mRNA transcript and releasing a Y-branched RNA composed of intron and distal SLRNA sequences (Sharp, 1987).

The presently disclosed subject matter involves engineering SL-addition trans-splicing to become a useful molecular tool for biological researchers. Because of the ubiquitous use of trans-splicing in lower metazoans, these novel methodologies are immediately useful in dozens of (mostly parasitic) organisms of biomedical, agricultural, and environmental interest. SL-addition trans-splicing can be adapted as a research tool in research organisms that normally do not perform SL-addition trans-splicing, such as vertebrate animals. These methodologies can provide innovative and unique products (cDNA libraries, biochips, etc.), services (transgenic production, cDNA synthesis, gene cloning), and devices (genotyping, molecular diagnostics).

Figure 2:
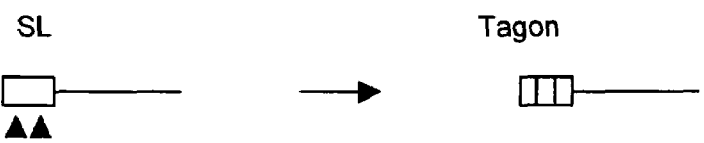
FIGS. 2A-2D schematically depict four representative strategies for introducing detectable alterations into a spliced leader sequence.
Figure 2:
Figure 2:
Figure 2:
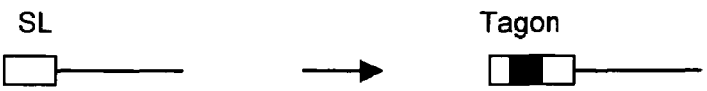

To genetically engineer SL-addition trans-splicing, synthetic sequences are inserted adjacent to or within the spliced leader mini-exon. Alternatively, the SL sequence can be mutated entirely. In keeping with the nomenclature exon and intron, the synthetic RNA sequences that are "tagged on" to the 5'-end of genes in a SL-addition trans-splicing reaction are designated "Tagon" sequences, and the genes that donate them as "Tagon-SLRNA" genes (FIG. 2).

When Tagon-SLRNAs are spliced onto mRNAs, the Tagon sequence can be used to purify expressed genes by simple oligonucleotide-mediated hybridization. These isolated mRNAs can be used to generate cDNA libraries, or directly labeled with fluorescent and/or radioactive tags for use as a probe in microarray studies. Alternatively, Tagon trans-spliced mRNAs can be specifically cloned by priming second-strand cDNA synthesis in a rapid amplification of cDNA ends (RACE) reaction using a designed oligonucleotide corresponding to the synthetic Tagon sequence.

To facilitate the recovery of subsets of expressed genes from defined tissues and/or cells, the Tagon-SLRNA gene is cloned downstream of a known cell type-specific or tissue-specific gene promoter. Tagon-SLRNA genes can be co-expressed with reporter genes driven by the same promoter (e.g., GFP), to visually confirm proper expression. These engineered constructs and novel methodologies provide tissue-specific cDNA libraries and enable tissue-specific profiling in organisms previously refractory to these analyses.

In some embodiments, the methodologies disclosed herein are employed in the model organism *C. elegans*, in which SL trans-splicing has been extensively characterized. Approximately 70% of the genes in *C. elegans* are trans-spliced. *C. elegans* has numerous well-defined tissue-specific promoters and numerous characterized mutants useful for cellular analysis. See e.g., Professor Shawn Lockery's homepage accessible from the University of Oregon's website.

II. Definitions

Unless otherwise defined, all technical and scientific terms used herein have the same meaning as commonly understood by one of ordinary skill in the art to which the presently disclosed subject matter pertains. For clarity of the present specification, certain definitions are presented herein below.

Following long-standing patent law convention, the terms "a" and "an" mean "one or more" when used in this application, including in the claims.

As used herein, the term "about", when referring to a value or to an amount of mass, weight, time, volume, concentration or percentage is meant to encompass variations of ±20% or ±10%, in another example ±5%, in another example ±1%, and in still another example ±0.1% from the specified amount, as such variations are appropriate to practice the presently disclosed subject matter. Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the terms "amino acid" and "amino acid residue" are used interchangeably and refer to any of the twenty naturally occurring amino acids, as well as analogs, derivatives, and congeners thereof; amino acid analogs having variant side chains; and all stereoisomers of any of any of the foregoing. Thus, the term "amino acid" is intended to embrace all molecules, whether natural or synthetic, which include both an amino functionality and an acid functionality and capable of being included in a polymer of naturally occurring amino acids.

An amino acid is formed upon chemical digestion (hydrolysis) of a polypeptide at its peptide linkages. The amino acid residues described herein are In some embodiments in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature abbreviations for amino acid residues are shown in tabular form presented hereinabove.

It is noted that all amino acid residue sequences represented herein by formulae have a left-to-right orientation in the conventional direction of amino terminus to carboxy terminus. In addition, the phrases "amino acid" and "amino acid residue" are broadly defined to include modified and unusual amino acids.

Furthermore, it is noted that a dash at the beginning or end of an amino acid residue sequence indicates a peptide bond to a further sequence of one or more amino acid residues or a covalent bond to an amino-terminal group such as $NH_2$ or acetyl or to a carboxy-terminal group such as COOH.

As used herein, the terms "associated with" and "operatively linked" refer to two nucleic acid sequences that are related physically or functionally. For example, a promoter or regulatory DNA sequence is said to be "associated with" a DNA sequence that encodes an RNA or a polypeptide if the two sequences are operatively linked, or situated such that the regulator DNA sequence will affect the expression level of the coding or structural DNA sequence.

As used herein, the terms "coding sequence" and "open reading frame" (ORF) are used interchangeably and refer to a nucleic acid sequence that is transcribed into RNA such as mRNA, rRNA, tRNA, snRNA, sense RNA, or antisense RNA. In some embodiments, the RNA is then translated in vivo or in vitro to produce a polypeptide.

As used herein, the term "complementary" refers to two nucleotide sequences that comprise anti-parallel nucleotide sequences capable of pairing with one another upon formation of hydrogen bonds between the complementary base residues in the anti-parallel nucleotide sequences. As is known in the art, the nucleic acid sequences of two complementary strands are the reverse complement of each other when each is viewed in the 5' to 3' direction.

As is also known in the art, two sequences that hybridize to each other under a given set of conditions do not necessarily have to be 100% fully complementary. As used herein, the terms "fully complementary" and "100% complementary" refer to sequences for which the complementary regions are 100% in Watson-Crick base-pairing; i.e., that no mismatches occur within the complementary regions. However, as is often the case with recombinant molecules (for example, cDNAs) that are cloned into cloning vectors, certain of these molecules can have non-complementary overhangs on either the 5' or 3' ends that result from the cloning event. In such a situation, it is understood that the region of 100% or full complementarity excludes any sequences that are added to the recombinant molecule (typically at the ends) solely as a result of, or to facilitate, the cloning event. Such sequences are, for example, polylinker sequences, linkers with restriction enzyme recognition sites, etc.

As used herein, the term "expression cassette" refers to a nucleic acid molecule capable of directing expression of a particular nucleotide sequence in an appropriate host cell, comprising a promoter operatively linked to the nucleotide sequence of interest which is operatively linked to termination signals. It also typically comprises sequences required for proper translation of the nucleotide sequence. The coding region usually encodes a polypeptide of interest but can also encode a functional RNA of interest, for example antisense RNA or a non-translated RNA, in the sense or antisense direction. The expression cassette comprising the nucleotide sequence of interest can be chimeric, meaning that at least one of its components is heterologous with respect to at least one of its other components. The expression cassette can also be one that is naturally occurring but has been obtained in a recombinant form useful for heterologous expression. Typically, however, the expression cassette is heterologous with respect to the host; i.e., the particular DNA sequence of the expression cassette does not occur naturally in the host cell and was introduced into the host cell or an ancestor of the host cell by a transformation event. The expression of the nucleotide sequence in the expression cassette can be under the control of a constitutive promoter or of an inducible promoter that initiates transcription only when the host cell is exposed to some particular external stimulus. In the case of a multicellular organism such as a plant, the promoter can also be specific to a particular tissue, organ, or stage of development.

As used herein, the term "fragment" refers to a sequence that comprises a subset of another sequence. When used in the context of a nucleic acid or amino acid sequence, the terms "fragment" and "subsequence" are used interchangeably. A fragment of a nucleic acid sequence can be any number of nucleotides that is less than that found in another nucleic acid sequence, and thus includes, but is not limited to, the sequences of an exon or intron, a promoter, an enhancer, an origin of replication, a 5' or 3' untranslated region, a coding region, and a polypeptide binding domain. It is understood that a fragment or subsequence can also comprise less than the entirety of a nucleic acid sequence, for example, a portion of an exon or intron, promoter, enhancer, etc. Similarly, a fragment or subsequence of an amino acid sequence can be any number of residues that is less than that found in a naturally occurring polypeptide, and thus includes, but is not limited to, domains, features, repeats, etc. Also similarly, it is understood that a fragment or subsequence of an amino acid sequence need not comprise the entirety of the amino acid sequence of the domain, feature, repeat, etc. A fragment can also be a "functional fragment", in which the fragment retains a specific biological function of the nucleic acid sequence or amino acid sequence of interest. For example, a functional fragment of a transcription factor can include, but is not limited to, a DNA binding domain, a transactivating domain, or both. Similarly, a functional fragment of a receptor tyrosine kinase includes, but is not limited to a ligand binding domain, a kinase domain, an ATP binding domain, and combinations thereof.

As used herein, the term "gene" refers to a nucleic acid that encodes an RNA, for example, nucleic acid sequences including, but not limited to, structural genes encoding a polypeptide or genes encoding an SLRNA. The term "gene" also refers broadly to any segment of DNA associated with a biological function. As such, the term "gene" encompasses sequences including, but not limited to a coding sequence, a promoter region, a transcriptional regulatory sequence, a non-expressed DNA segment that is a specific recognition sequence for regulatory proteins, a non-expressed DNA segment that contributes to gene expression, a DNA segment designed to have desired parameters, or combinations thereof. A gene can be obtained by a variety of methods, including cloning from a biological sample, synthesis based on known or predicted sequence information, and recombinant derivation from one or more existing sequences.

As is understood in the art, a gene comprises a coding strand and a non-coding strand. As used herein, the terms "coding strand" and "sense strand" are used interchangeably, and refer to a nucleic acid sequence that has the same sequence of nucleotides as an mRNA from which the gene product is translated. As is also understood in the art, when the coding strand and/or sense strand is used to refer to a DNA molecule, the coding/sense strand includes thymidine residues instead of the uridine residues found in the corresponding mRNA. Additionally, when used to refer to a DNA molecule, the coding/sense strand can also include additional elements not found in the mRNA including, but not limited to promoters, enhancers, and introns. Similarly, the terms "template strand" and "antisense strand" are used interchangeably and refer to a nucleic acid sequence that is complementary to the coding/sense strand.

The term "gene expression" generally refers to the cellular processes by which a biologically active polypeptide is produced from a DNA sequence and exhibits a biological activity in a cell. As such, gene expression involves the processes of transcription and translation, but also involves post-transcriptional and post-translational processes that can influence a biological activity of a gene or gene product. These processes include, but are not limited to RNA syntheses, processing, and transport, as well as polypeptide synthesis, transport, and post-translational modification of polypeptides, either individually or in any combination of more than one. Additionally, processes that affect protein-protein interactions within the cell can also affect gene expression as defined herein.

The terms "heterologous", "recombinant", and "exogenous", when used herein to refer to a nucleic acid sequence (e.g., a DNA sequence) or a gene, refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling or other recombinant techniques (for example, cloning the gene into a vector). The terms also include non-naturally occurring multiple copies of a naturally occurring DNA sequence. Thus, the terms refer to a DNA segment that is foreign or heterologous to the cell, or homologous to the cell but in a position or form within the host cell in which the element is not ordinarily found. Similarly, when used in the context of a polypeptide or amino acid sequence, an exogenous polypeptide or amino acid sequence is a polypeptide or amino acid sequence that originates from a source foreign to the particular host cell or, if from the same source, is modified from its original form. Thus, exogenous DNA segments can be expressed to yield exogenous polypeptides.

A "homologous" or "endogenous" nucleic acid (or amino acid) sequence is a nucleic acid (or amino acid) sequence naturally associated with a host cell into which it is introduced.

The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. The phrase "hybridize(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

An "isolated" nucleic acid molecule or protein, or biologically active portion thereof, is substantially free of other cellular material, or culture medium when produced by recombinant techniques, or substantially free of chemical precursors or other chemicals when chemically synthesized. Thus, the term "isolated nucleic acid" refers to a polynucleotide of genomic, cDNA, or synthetic origin or some combination thereof, which (1) is not associated with the cell in which the "isolated nucleic acid" is found in nature, or (2) is operatively linked to a polynucleotide to which it is not linked in nature. Similarly, the term "isolated polypeptide" refers to a polypeptide, in certain embodiments prepared from recombinant DNA or RNA, or of synthetic origin, or some combination thereof, which (1) is not associated with proteins that it is normally found within nature, (2) is isolated from the cell in which it normally occurs, (3) is isolated free of other proteins from the same cellular source, (4) is expressed by a cell from a different species, or (5) does not occur in nature.

In certain embodiments, an "isolated" nucleic acid is free of sequences (e.g., protein encoding or regulatory sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of the nucleotide sequences that naturally flank the nucleic acid molecule in genomic DNA of the cell from which the nucleic acid is derived. A protein that is substantially free of cellular material includes preparations of protein or polypeptide having less than about 30%, 20%, 10%, or 5%, (by dry weight) of contaminating protein. When the protein of the presently disclosed subject matter, or biologically active portion thereof, is recombinantly produced, culture medium represents less than about 30%, 20%, 10%, or 5% (by dry weight) of chemical precursors or non-protein of interest chemicals. Thus, the term "isolated", when used in the context of an isolated DNA molecule or an isolated polypeptide, refers to a DNA molecule or polypeptide that, by the hand of man, exists apart from its native environment and is therefore not a product of nature. An isolated DNA molecule or polypeptide can exist in a purified form or can exist in a non-native environment such as, for example, in a transgenic host cell.

The term "isolated", when used in the context of an "isolated cell", refers to a cell that has been removed from its natural environment: for example, as a part of an organ, tissue, or organism.

As used herein, the term "mutation" carries its traditional connotation and refers to a change, inherited, naturally occurring or introduced, in a nucleic acid or polypeptide sequence, and is used in its sense as generally known to those of skill in the art.

As used herein, the terms "endogenous" and "native" refer to a gene that is naturally present in the genome of an untransformed cell or organism. Similarly, when used in the context of a polypeptide, a "native polypeptide" is a polypeptide that is encoded by a native gene of an untransformed cell's or organism's genome.

As used herein, the term "naturally occurring" refers to an object that is found in nature as distinct from being artificially produced by man. For example, a polypeptide or nucleotide sequence that is present in an organism (including a virus) in its natural state, which has not been intentionally modified or isolated by man in the laboratory, is naturally occurring. As such, a polypeptide or nucleotide sequence is considered "non-naturally occurring" if it is encoded by or present within a recombinant molecule, even if the amino acid or nucleic acid sequence is identical to an amino acid or nucleic acid sequence found in nature.

As used herein, the terms "nucleic acid" and "nucleic acid molecule" refer to any of deoxyribonucleic acid (DNA), ribonucleic acid (RNA), oligonucleotides, fragments generated by the polymerase chain reaction (PCR), and fragments generated by any of ligation, scission, endonuclease action, and exonuclease action. Nucleic acids can be composed of monomers that are naturally occurring nucleotides (such as deoxyribonucleotides and ribonucleotides), or analogs of naturally occurring nucleotides (e.g., α-enantiomeric forms of naturally occurring nucleotides), or a combination of both. Modified nucleotides can have modifications in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid" also includes so-called "peptide nucleic acids", which comprise naturally occurring or modified nucleic acid bases attached to a polyamide backbone. Nucleic acids can be either single stranded or double stranded.

The term "operatively linked", when describing the relationship between two nucleic acid regions, refers to a juxtaposition wherein the regions are in a relationship permitting them to function in their intended manner. For example, a control sequence "operatively linked" to a coding sequence is ligated in such a way that expression of the coding sequence is achieved under conditions compatible with the control sequences, such as when the appropriate molecules (e.g., inducers and polymerases) are bound to the control or regulatory sequence(s). Thus, in some embodiments, the phrase "operatively linked" refers to a promoter connected to a coding sequence in such a way that the transcription of that coding sequence is controlled and regulated by that promoter. Techniques for operatively linking a promoter to a coding sequence are well known in the art; the precise orientation and location relative to a coding sequence of interest is dependent, inter alia, upon the specific nature of the promoter.

Thus, the term "operatively linked" can refer to a promoter region that is connected to a nucleotide sequence in such a way that the transcription of that nucleotide sequence is controlled and regulated by that promoter region. Similarly, a nucleotide sequence is said to be under the "transcriptional control" of a promoter to which it is operatively linked. Techniques for operatively linking a promoter region to a nucleotide sequence are known in the art. The term "operatively linked" can also refer to a transcription termination sequence or other nucleic acid that is connected to a nucleotide sequence in such a way that termination of transcription of that nucleotide sequence is controlled by that transcription termination sequence. Additionally, the term "operatively linked" can refer to an enhancer, silencer, or other nucleic acid regulatory sequence that when operatively linked to an open reading frame modulates the expression of that open reading frame, either in a positive or negative fashion.

"Stringent hybridization conditions" and "stringent hybridization wash conditions" in the context of nucleic acid hybridization experiments such as Southern and Northern blot analysis are both sequence- and environment-dependent. Longer sequences hybridize specifically at higher temperatures. An extensive guide to the hybridization of nucleic acids is found in Tijssen, 1993. Generally, high stringency hybridization and wash conditions are selected to be about 5° C. lower than the thermal melting point ($T_m$) for the specific sequence at a defined ionic strength and pH. Typically, under "highly stringent conditions" a probe will hybridize specifically to its target subsequence, but to no other sequences. Similarly, medium stringency hybridization and wash conditions are selected to be more than about 5° C. lower than the $T_m$ for the specific sequence at a defined ionic strength and pH. Exemplary medium stringency conditions include hybridizations and washes as for high stringency conditions, except that the temperatures for the hybridization and washes are in some embodiments 8° C., in some embodiments 10° C., in some embodiments 12° C., and in some embodiments 15° C. lower than the $T_m$ for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of highly stringent hybridization conditions for Southern or Northern Blot analysis of complementary nucleic acids having more than about 100 complementary residues is overnight hybridization in 50% formamide with 1 mg of heparin at 42° C. An example of highly stringent wash conditions is 15 minutes in 0.1× standard saline citrate (SSC), 0.1% (w/v) SDS at 65° C. Another example of highly stringent wash conditions is 15 minutes in 0.2×SSC buffer at 65° C. (see Sambrook et al., 2001 for a description of SSC buffer and other stringency conditions) (Sambrook and Russell 2001). Often, a high stringency wash is preceded by a lower stringency wash to remove background probe signal. An example of medium stringency wash conditions for a duplex of more than about 100 nucleotides is 15 minutes in 1×SSC at 45° C. Another example of medium stringency wash for a duplex of more than about 100 nucleotides is 15 minutes in 4-6×SSC at 40° C. For short probes (e.g., about 10 to 50 nucleotides), stringent conditions typically involve salt concentrations of less than about 1M $Na^+$ ion, typically about 0.01 to 1M $Na^+$ ion concentration (or other salts) at pH 7.0-8.3, and the temperature is typically at least about 30° C. Stringent conditions can also be achieved with the addition of destabilizing agents such as formamide. In general, a signal to noise ratio of 2-fold (or higher) than that observed for an unrelated probe in the particular hybridization assay indicates detection of a specific hybridization.

The following are examples of hybridization and wash conditions that can be used to clone homologous nucleotide sequences that are substantially similar to reference nucleotide sequences of the presently disclosed subject matter a probe nucleotide sequence hybridizes in one example to a target nucleotide sequence in 7% sodium dodecyl sulfate (SDS), 0.5M $NaPO_4$, 1 mm ethylenediamine tetraacetic acid (EDTA) at 50° C. followed by washing in 2×SSC, 0.1% SDS at 50° C.; in another example, a probe and target sequence hybridize in 7% SDS, 0.5 M $NaPO_4$, 1 mm EDTA at 50° C. followed by washing in 1×SSC, 0.1% SDS at 50° C.; in another example, a probe and target sequence hybridize in 7% SDS, 0.5 M $NaPO_4$, 1 mm EDTA at 50° C. followed by washing in 0.5×SSC, 0.1% SDS at 50° C.; in another example, a probe and target sequence hybridize in 7% SDS, 0.5 M $NaPO_4$, 1 mm EDTA at 50° C. followed by washing in 0.1×SSC, 0.1% SDS at 50° C.; in yet another example, a probe and target sequence hybridize in 7% SDS, 0.5 M $NaPO_4$, 1 mm EDTA at 50° C. followed by washing in 0.1×SSC, 0.1% SDS at 65° C. In some embodiments, hybridization conditions comprise hybridization in a roller tube for at least 12 hours at 42° C.

The term "phenotype" refers to the entire physical, biochemical, and physiological makeup of a cell or an organism; e.g., having any one trait or any group of traits. As such, phenotypes result from the expression of genes within a cell or an organism, and relate to traits that are potentially observable or assayable.

As used herein, the terms "polypeptide", "protein", and "peptide", which are used interchangeably herein, refer to a polymer of the 20 protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides and proteins, unless otherwise noted. As used herein, the terms "protein", "polypeptide", and "peptide" are used interchangeably herein when referring to a gene product. The term "polypeptide" encompasses proteins of all functions, including enzymes. Thus, exemplary polypeptides include gene products, naturally occurring proteins, homologs, orthologs, paralogs, fragments, and other equivalents, variants and analogs of the foregoing.

The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both. Fragments typically are at least 5, 6, 8, or 10 amino acids long, at least 14 amino acids long, at least 20, 30, 40 or 50 amino acids long, at least 75 amino acids long, or at least 100, 150, 200, 300, 500 or more amino acids long. A fragment can retain one or more of the biological activities of the reference polypeptide. In certain embodiments, a fragment can comprise a domain or feature, and optionally additional amino acids on one or both sides of the domain or feature, which additional amino acids can number from 5, 10, 15, 20, 30, 40, 50, or up to 100 or more residues. Further, fragments can include a sub-fragment of a specific region, which sub-fragment retains a function of the region from which it is derived. In some embodiments, a fragment can have immunogenic properties.

As used herein, the term "pre-polypeptide" refers to a polypeptide that comprises a transit peptide that is post-translationally removed.

As used herein, the term "primer" refers to a sequence comprising in some embodiments two or more deoxyribonucleotides or ribonucleotides, in some embodiments more than three, in some embodiments more than eight, and in some embodiments at least about 20 nucleotides of an exonic or intronic region. Such oligonucleotides are in some embodiments between ten and thirty bases in length.

The term "promoter" or "promoter region" each refers to a nucleotide sequence within a gene that is positioned 5' to a coding sequence and functions to direct transcription of the coding sequence. The promoter region comprises a transcriptional start site, and can additionally include one or more transcriptional regulatory elements. In some embodiments, a method of the presently disclosed subject matter employs a tissue-specific or cell type-specific promoter.

As used herein, the term "minimal promoter" refers to the smallest piece of a promoter, such as a TATA element, that can support any transcription. A minimal promoter typically has greatly reduced promoter activity in the absence of upstream or downstream activation. In the presence of a suitable transcription factor, a minimal promoter can function to permit transcription. As such, a "minimal promoter" is a nucleotide sequence that has the minimal elements required to enable basal level transcription to occur. Typically, minimal promoters are not necessarily complete promoters but rather can be subsequences of promoters that are capable of directing a basal level of transcription of a reporter construct in an experimental system. Minimal promoters include but are not limited to the cytomegalovirus (CMV) minimal promoter, the herpes simplex virus thymidine kinase (HSV-tk) minimal promoter, the simian virus 40 (SV40) minimal promoter, the human beta-actin minimal promoter, the human EF2 minimal promoter, the adenovirus E1B minimal promoter, and the heat shock protein (hsp) 70 minimal promoter. Minimal promoters are often augmented with one or more transcriptional regulatory elements to influence the transcription of an operatively linked gene. For example, cell-type-specific or tissue-specific transcriptional regulatory elements can be added to minimal promoters to create recombinant promoters that direct transcription of an operatively linked nucleotide sequence in a cell-type-specific or tissue-specific manner Different promoters have different combinations of transcriptional regulatory elements. Whether or not a gene is expressed in a cell is dependent on a combination of the particular transcriptional regulatory elements that make up the gene's promoter and the different transcription factors that are present within the nucleus of the cell. As such, promoters are often classified as "constitutive", "tissue-specific", "cell-type-specific", or "inducible", depending on their functional activities in vivo or in vitro. For example, a constitutive promoter is one that is capable of directing transcription of a gene in a variety of cell types. Exemplary constitutive promoters include the promoters for the following genes which encode certain constitutive or "housekeeping" functions: hypoxanthine phosphoribosyl transferase (HPRT), dihydrofolate reductase (DHFR) (Scharfmann, Axelrod et al. 1991); adenosine deaminase, phosphoglycerate kinase (PGK), pyruvate kinase, phosphoglycerate mutase, the β-actin promoter (Williams, Thomas et al. 1993), and other constitutive promoters known to those of skill in the art. "Tissue-specific" or "cell-type-specific" promoters, on the other hand, direct transcription in some tissues and cell types but are inactive in others. Exemplary tissue-specific promoters include those promoters described in more detail herein below, as well as other tissue-specific and cell-type specific promoters known to those of skill in the art.

When used in the context of a promoter, the term "linked" as used herein refers to a physical proximity of promoter elements such that they function together to direct transcription of an operatively linked nucleotide sequence.

The term "transcriptional regulatory sequence" or "transcriptional regulatory element", as used herein, each refers to a nucleotide sequence within the promoter region that enables responsiveness to a regulatory transcription factor. Responsiveness can encompass a decrease or an increase in transcriptional output and is mediated by binding of the transcription factor to the DNA molecule comprising the transcriptional regulatory element. In some embodiments, a transcriptional regulatory sequence is a transcription termination sequence, alternatively referred to herein as a transcription termination signal.

The term "transcription factor" generally refers to a protein that modulates gene expression by interaction with the transcriptional regulatory element and cellular components for transcription, including RNA Polymerase, Transcription Associated Factors (TAFs), chromatin-remodeling proteins, and any other relevant protein that impacts gene transcription.

As used herein, "significance" or "significant" relates to a statistical analysis of the probability that there is a non-random association between two or more entities. To determine whether or not a relationship is "significant" or has "significance", statistical manipulations of the data can be performed to calculate a probability, expressed as a "p-value". Those p-values that fall below a user-defined cutoff point are regarded as significant. In one example, a p-value less than or equal to 0.05, in another example less than 0.01, in another example less than 0.005, and in yet another example less than 0.001, are regarded as significant.

The term "purified" refers to an object species that is the predominant species present (i.e., on a molar basis it is more abundant than any other individual species in the composition). A "purified fraction" is a composition wherein the object species comprises at least about 50 percent (on a molar basis) of all species present. In making the determination of the purity of a species in solution or dispersion, the solvent or matrix in which the species is dissolved or dispersed is usually not included in such determination; instead, only the species (including the one of interest) dissolved or dispersed are taken into account. Generally, a purified composition will have one species that comprises more than about 80 percent of all species present in the composition, more than about 85%, 90%, 95%, 99% or more of all species present. The object species can be purified to essential homogeneity (contaminant species cannot be detected in the composition by conventional detection methods) wherein the composition consists essentially of a single species. A skilled artisan can purify a polypeptide of the presently disclosed subject matter using standard techniques for protein purification in light of the teachings herein. Purity of a polypeptide can be determined by a number of methods known to those of skill in the art, including for example, amino-terminal amino acid sequence analysis, gel electrophoresis, and mass-spectrometry analysis.

The terms "regulatory sequence" and "regulatory elements" are generic terms used throughout the specification to refer to polynucleotide sequences, such as initiation signals, enhancers, regulators, promoters (including minimal promoters), and termination sequences, which are necessary or desirable to affect the expression of coding and non-coding sequences to which they are operatively linked. Regulatory elements can comprise a promoter operatively linked to the nucleotide sequence of interest and termination signals. Exemplary regulatory sequences are described in Goeddel, 1990, and include, for example, the early and late promoters of simian virus 40 (SV40), adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase; e.g., Pho5, the promoters of the yeast a-mating factors, the polyhedron promoter of the baculovirus system and other sequences known to control the expression of genes of prokaryotic or eukaryotic cells or their viruses, and various combinations thereof (Goeddel 1990). The nature and use of such control sequences can differ depending upon the host organism. In prokaryotes, such regulatory sequences generally include promoter, ribosomal binding site, and transcription termination sequences. The term "regulatory sequence" is intended to include, at a minimum, components whose presence can influence expression, and can also include additional components whose presence is advantageous, for example, leader sequences and fusion partner sequences.

In certain embodiments, transcription of a polynucleotide sequence is under the control of a promoter sequence (or other regulatory sequence) that controls the expression of the polynucleotide in a cell-type in which expression is intended. It will also be understood that the polynucleotide can be under the control of regulatory sequences that are the same or different from those sequences which control expression of the naturally occurring form of the polynucleotide.

The term "reporter gene" refers to a nucleic acid comprising a nucleotide sequence encoding a protein that is readily detectable either by its presence or activity, including, but not limited to, luciferase, fluorescent protein (e.g., green fluorescent protein), chloramphenicol acetyl transferase, β-galactosidase, secreted placental alkaline phosphatase, β-lactamase, human growth hormone, and other secreted enzyme reporters. Generally, a reporter gene encodes a polypeptide not otherwise produced by the host cell, which is detectable by analysis of the cell(s); e.g., by the direct fluorometric, radioisotopic or spectrophotometric analysis of the cell(s) and typically without the need to kill the cells for signal analysis. In certain instances, a reporter gene encodes an enzyme, which produces a change in fluorometric properties of the host cell, which is detectable by qualitative, quantitative, or semiquantitative function or transcriptional activation. Exemplary enzymes include esterases, β-lactamase, phosphatases, peroxidases, proteases (tissue plasminogen activator or urokinase) and other enzymes whose function can be detected by appropriate chromogenic or fluorogenic substrates known to those skilled in the art or developed in the future.

As used herein, the term "sequencing" refers to determining the ordered linear sequence of nucleic acids or amino acids of a DNA or protein target sample, using conventional manual or automated laboratory techniques.

As used herein, the term "substantially pure" refers to that the polynucleotide or polypeptide is substantially free of the sequences and molecules with which it is associated in its natural state, and those molecules used in the isolation procedure. The term "substantially free" refers to that the sample is in some embodiments at least 50%, in some embodiments at least 70%, in some embodiments 80%, and in some embodiments 90% free of the materials and compounds with which is it associated in nature.

As used herein, the term "target cell" refers to a cell, into which it is desired to insert a nucleic acid sequence or polypeptide, or to otherwise effect a modification from conditions known to be standard in the unmodified cell. A nucleic acid sequence introduced into a target cell can be of variable length. Additionally, a nucleic acid sequence can enter a target cell as a component of a plasmid or other vector or as a naked sequence.

As used herein, the term "transcription" refers to a cellular process involving the interaction of an RNA polymerase with a gene that directs the expression as RNA of the structural information present in the coding sequences of the gene. The process includes, but is not limited to, the following steps: (a) the transcription initiation; (b) transcript elongation; (c) transcript splicing; (d) transcript capping; (e) transcript termination; (f) transcript polyadenylation; (g) nuclear export of the transcript; (h) transcript editing; and (i) stabilizing the transcript.

As used herein, the term "transcription factor" refers to a cytoplasmic or nuclear protein which binds to a gene, or binds to an RNA transcript of a gene, or binds to another protein which binds to a gene or an RNA transcript or another protein which in turn binds to a gene or an RNA transcript, so as to thereby modulate expression of the gene. Such modulation can additionally be achieved by other mechanisms; the essence of a "transcription factor for a gene" pertains to a factor that alters the level of transcription of the gene in some way.

The term "transfection" refers to the introduction of a nucleic acid; e.g., an expression vector, into a recipient cell, which in certain instances involves nucleic acid-mediated gene transfer. The term "transformation" refers to a process in which a cell's genotype is changed as a result of the cellular uptake of exogenous nucleic acid. For example, a transformed cell can express a recombinant form of a polypeptide of the presently disclosed subject matter or antisense expression can occur from the transferred gene so that the expression of a naturally occurring form of the gene is disrupted.

The term "vector" refers to a nucleic acid capable of transporting another nucleic acid to which it has been linked. One type of vector that can be used in accord with the presently disclosed subject matter is an episome; i.e., a nucleic acid capable of extra-chromosomal replication. Other vectors include those capable of autonomous replication and expression of nucleic acids to which they are linked. Vectors capable of directing the expression of genes to which they are operatively linked are referred to herein as "expression vectors". In general, expression vectors of utility in recombinant DNA techniques are often in the form of plasmids. In the present specification, "plasmid" and "vector" are used interchangeably as the plasmid is the most commonly used form of vector. However, the presently disclosed subject matter is intended to include such other forms of expression vectors which serve equivalent functions and which become known in the art subsequently hereto.

The term "expression vector" as used herein refers to a DNA sequence capable of directing expression of a particular nucleotide sequence in an appropriate host cell, comprising a promoter operatively linked to the nucleotide sequence of interest which is operatively linked to transcription termination sequences. It also typically comprises sequences required for proper translation of the nucleotide sequence. The construct comprising the nucleotide sequence of interest can be chimeric. The construct can also be one that is naturally occurring but has been obtained in a recombinant form useful for heterologous expression. The nucleotide sequence of interest, including any additional sequences designed to effect proper expression of the nucleotide sequences, can also be referred to as an "expression cassette".

The terms "heterologous gene", "heterologous DNA sequence", "heterologous nucleotide sequence", "exogenous nucleic acid molecule", or "exogenous DNA segment", as used herein, each refer to a sequence that originates from a source foreign to an intended host cell or, if from the same source, is modified from its original form. Thus, a heterologous gene in a host cell includes a gene that is endogenous to the particular host cell but has been modified, for example by mutagenesis or by isolation from native transcriptional regulatory sequences. The terms also include non-naturally occurring multiple copies of a naturally occurring nucleotide sequence. Thus, the terms refer to a DNA segment that is foreign or heterologous to the cell, or homologous to the cell but in a position within the host cell nucleic acid wherein the element is not ordinarily found.

Two nucleic acids are "recombined" when sequences from each of the two nucleic acids are combined in a progeny nucleic acid. Two sequences are "directly" recombined when both of the nucleic acids are substrates for recombination. Two sequences are "indirectly recombined" when the sequences are recombined using an intermediate such as a cross over oligonucleotide. For indirect recombination, no more than one of the sequences is an actual substrate for recombination, and in some cases, neither sequence is a substrate for recombination.

As used herein, the terms "transformed", "transgenic", and "recombinant" refer to a host organism such as a bacterium, animal, or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism; e.g., a bacterium or plant, which does not contain the heterologous nucleic acid molecule.

By "transgenic animal" is meant a non-human animal, usually a mammal (e.g., mouse, rat, rabbit, hamster, etc.), having a non-endogenous (i.e., heterologous) nucleic acid sequence present as an extrachromosomal element in a portion of its cells or stably integrated into its germ line DNA (i.e., in the genomic sequence of most or all of its cells). A heterologous nucleic acid is introduced into the germ line of such transgenic animals by genetic manipulation of, for example, embryos or embryonic stem cells of the host animal.

A "knock-out" of a gene means an alteration in the sequence of the gene that results in a decrease of function of the target gene, in some embodiments such that target gene expression is undetectable or insignificant in a cell, tissue, or organism. A knock-out of an endogenous SLRNA gene means that function of one or more endogenous SLRNA gene has been substantially decreased so that expression is not detectable or only present at insignificant levels. "Knock-out" transgenics can be transgenic animals having a heterozygous knock-out of an endogenous SLRNA gene or a homozygous knock-out of an endogenous SLRNA gene. "Knock-outs" also include conditional knock-outs, where alteration of the target gene can occur upon, for example, exposure of the animal to a substance that promotes target gene alteration, introduction of an enzyme that promotes recombination at the target gene site (e.g., the Cre in the Cre-lox system), or other method for directing the target gene alteration postnatally.

A "knock-in" of a target gene means an alteration in a host cell genome that results in altered expression (e.g., increased (including ectopic)) of the target gene, for example by introduction of an additional copy of the target gene, or by operatively inserting a regulatory sequence that provides for enhanced expression of an endogenous copy of the target gene. "Knock-in" transgenics of interest for the presently disclosed subject matter can be transgenic animals having a knock-in of one or more of the animal's endogenous SLRNA genes. Such transgenics can be heterozygous for a knock-in of an SLRNA gene or homozygous for a knock-in of an SLRNA gene. "Knock-ins" also encompass conditional knock-ins as defined above.

Techniques for the preparation of transgenic animals are known in the art. Exemplary techniques are described for transgenic rats (U.S. Pat. No. 5,489,742); transgenic mice (U.S. Pat. Nos. 4,736,866, 5,550,316, 5,614,396, 5,625,125 and 5,648,061); transgenic pigs (U.S. Pat. No. 5,973,933); U.S. Pat. No. 5,162,215 (transgenic avian species), U.S. Pat. No. 5,741,957 (transgenic bovine species), and (Stinchcomb, Shaw et al. 1985; Mello, Kramer et al. 1991; Mello and Fire 1995) (transgenic worms).

Briefly, nucleotide sequences of interest are cloned into a vector (e.g., pLNK; Gorman et al., 1996), and the construct is transformed into a germ cell. In the germ cell, a chromosomal rearrangement event takes place wherein the nucleic acid sequences of interest are integrated into the genome of the germ cell by homologous recombination (Gorman, van der Stoep et al. 1996). Fertilization and propagation of the transformed germ cell results in a transgenic animal. Homozygosity of the mutation is accomplished by intercrossing.

III. Splicing Generally

In vitro analysis of cis-splicing demonstrated no obligate requirement for the 5' and 3' splice sites to be on a single, contiguous RNA molecule (Konarska, Padgett et al. 1985; Solnick 1985). These results suggested that trans-splicing might be a common cellular mechanism in the maturation of mRNAs. Evidence for trans-splicing was shown in 1986 in trypanosomes (Sutton and Boothroyd 1986). A novel Y-branched structure was seen as a splicing intermediate and/or intronic product, analogous to the lariat RNA structure seen cis-splicing (Murphy, Watkins et al. 1986). Soon after, trans-splicing was detected in the nematode *C. elegans* (Krause and Hirsh 1987). A 22-nucleotide "leader" sequence was found spliced at the 5' end of actin mRNA, and this sequence was found to be donated from a gene in an entirely different chromosomal location, a Spliced leader RNA gene (SLRNA). Trans-splicing was shown to be capable of producing multiple mRNAs by the discovery of alternative trans-splicing in trypanosomes. Trypanosomes were shown to utilize 2'-5' branches and to possess a debranching activity (Sutton and Boothroyd 1988). Trans splicing was shown to most resemble cis-splicing by the identification of ribonucleoprotein complexes containing the spliced leader RNAs (Thomas, Conrad et al. 1988; Van Doren and Hirsh 1988), and U2 equivalent RNAs as distinct particles (Michaeli, Roberts et al. 1990). *C. elegans* mRNAs are shown to acquire a spliced leader through a trans-splicing mechanism (Bektesh and Hirsh 1988). *C. elegans* trans-spliced leader RNA is bound to Sm and has a trimethylguanosine cap (Thomas, Conrad et al. 1988; Liou and Blumenthal 199b).

A Spliced Leader sequence (SL1) first discovered on actin mRNA in *C. elegans* is found on different mRNAs and in different genera of nematodes (Bektesh, Van Doren et al. 1988). The same spliced leader is found in the human parasitic nematode *Brugia malayi* (Takacs, Denker et al. 1988). Trans-splicing is also found in *Leishmania* (Bard 1989). A spliced leader is present on a subset of mRNAs from the human parasite *Schistosoma mansoni* (Rajkovic, Davis et al. 1990). *Onchocerca volvulus* has trans-spliced actin genes (Zeng and Donelson 1992). Trans-splicing was discovered in the protist *Euglena* (Tessier, Keller et al. 1991). Trans-splicing is found in cnidarians (Stover and Steele 2001). Finally, trans-splicing was recently discovered in the chordates (Vandenberghe, Meedel et al. 2001) In vitro transcription of SLRNA gene is found to be dependent on the DNA primary sequence of the leader 22mer, indicating that it acts as a transcribed, internal promoter element (Maroney, Hannon et al. 1990). Nematode trans-splicing in vitro was shown to be insensitive to nucleotide changes and/or deletions in the conserved spliced leader sequence (Hannon, Maroney et al. 1990). Molecular techniques show the insertion of part of an intron into the 5'-untranslated region (5'-UTR) of a *C. elegans* gene converts it into a trans-spliced gene (Conrad, Thomas et al. 1991). Intramolecular base pairing between the nematode spliced leader and its 5' splice site is not essential for trans splicing in vitro (Maroney, Hannon et al. 1991).

While operons are found to be a common form of chromosomal organization in *C. elegans* (Zorio, Cheng et al. 1994), the function of the SL primary sequence in splicing remains enigmatic. Variability in sequence is seen. In vivo structural analysis of spliced leader RNAs in *trypanosoma* and *leptomonas* shows the SL RNA to be a flexible structure (Harris, Crothers et al. 1995). Trans-splicing is seen in flatworms (Davis, Hardwick et al. 1995); Davis, 1997), and the spliced leaders are surprisingly diverse (Davis 1997). *Onchocerca volvulus* uses novel spliced leader (Da'Dara, Henkle-Duhrsen et al. 1996). Structure-function analysis of unicellular trypanosomid spliced leader RNAs indicated that exon mutations were not trans-spliced (Goncharov, Xu et al. 1998). However, trans-splicing of mutated spliced leader exons in *Leishmania tarentolae* is found to be efficient (Sturm, Fleischmann et al. 1998).

Research by Rubin and colleagues have revealed variability in the length and sequence of Spliced Leaders in *C. elegans*. Endogenous Spliced Leader addition of 21 and 23 nucleotides have been observed (Ross, Freedman et al. 1995). Expression of these minor spliced leaders may acquire tissue-specific expression. For example, SL4 is a spliced leader that appears to have preferential expression in the hypodermis (Ross, Freedman et al. 1995).

Numerous mutational studies have been conducted to determine conserved elements of Spliced Leaders SL1 and SL2. Deletion of the genomic locus for spliced leaders, located in a conserved array with 5S RNA genes, revealed an important element for SLRNA gene (Ferguson, Heid et al. 1996).

Mutational studies of SL1 thus far have been unable to reveal distinct conserved 'blocks' of RNA mini-exon sequence required for RNA splicing and/or translation. Small insertions in SL1 mutating the leader to a 20-25 nucleotide sequence has little deleterious effect on viability (Xie and Hirsh 1998; Ferguson and Rothman 1999).

IV. Applications

The presently disclosed subject matter provides methods for isolating a trans-spliced ribonucleic acid (RNA) molecule. In some embodiments, the method comprises (a) introducing into the cell a nucleic acid molecule encoding a derivatized spliced leader RNA (SLRNA) molecule, wherein the derivatized SLRNA molecule comprises a spliced leader sequence comprising a unique sequence; (b) expressing the derivatized SLRNA in the cell, wherein the expressing results in the spliced leader sequence being trans-spliced onto the ribonucleic acid molecule; and (c) isolating the trans-spliced ribonucleic acid molecule comprising the spliced leader sequence. In some embodiments, the present method further comprises sequencing the trans-spliced ribonucleic acid molecule or a reverse transcription product thereof.

In some embodiments, a nucleic acid molecule encoding a derivatized SLRNA molecule is introduced into a cell. As used herein, the term "introduce", and grammatical variations thereof, refers to a manipulation of the cell whereby an exogenous nucleic acid molecule (for example, a nucleic acid molecule encoding a derivatized SLRNA) enters the cell and is expressed therein. Consistent with the present method, the exact nature of the manipulation is not limiting, and the nucleic acid molecule can be introduced by any technique known in the art. One exemplary technique for introducing nucleic acid molecules into cells is by microinjection, such as using the technique disclosed in (Stinchcomb, Shaw et al. 1985; Mello, Kramer et al. 1991; Mello and Fire 1995). Other techniques that can be used to introduce nucleic acid molecules into cells are disclosed on the C. elegans WWW Server maintained by Professor Leon Avery of the University of Texas Southwestern Medical Center at Dallas. Exemplary tissue- and cell-types that can be examined using the presently disclosed methods include, but are not limited to neuronal cells (including, but not limited to motor neurons, sensory neurons including mechanosensory, thermosensory and chemosensory, interneurons, ring neurons, serotonergic neurons, glutamatergic neurons, GABAergic neurons, dopaminergic neurons, and cholinergic neurons), endothelial cells, gonadal cells, gut cells, muscle cells, duct cells, sheath cells, pharyngeal cells, vulval cells, ray cells, labial cells, excretory cells, sperm, oocytes, and coelomocytes. Exemplary promoters that can be used to examine these cells types include the promoters for the C. elegans mec-3, lin-26, and vit-2/6 genes.

In some embodiments, the nucleic acid molecule can be introduced into a cell that is present within an organism.

As used herein, the term "derivatized" refers to an SLRNA comprising a nucleotide sequence that can be detected once expressed in the cell. In some embodiments, the derivatized SLRNA comprises a nucleotide sequence that can be detected. In this embodiment, the derivatized SLRNA is expressed from an exogenous (i.e. non-naturally occurring) gene into which a unique sequence has been introduced. In this embodiment, the term "unique" refers to a sequence present within the derivatized SLRNA gene that is not normally present in the spliced leader portion (SL) of an SLRNA gene. Such unique sequences can be any sequence of one or more nucleotides that allows the derivatized SLRNA molecule (and hence any RNA molecules to which the spliced leader encoded by the SLRNA molecule is trans-spliced) to be detected within the cell, tissue, organ, or organism, and/or isolated from the cell, tissue, organ, or organism. As such, the unique sequence can be produced by making one or more changes in the sequence of an endogenous SLRNA gene, such changes being selected from the group consisting of single base changes, insertions, deletions, inversions, etc. The only requirement for the nature of the derivatization is that the derivatized SLRNA gene encodes a spliced leader that is detectable by comprising a unique sequence as defined herein.

In some embodiments, the unique sequence differs from SL sequences naturally occurring in the species into which the derivatized SLRNA gene is introduced, by definition. In some embodiments, the unique sequence is introduced into species with no naturally occurring SL sequences. In some embodiments, the unique sequence is of a length and composition suitable for oligo-nucleotide hybridization. In some embodiments, the unique sequence is of a length and composition suitable for use as a primer-binding site for recognition and/or use by a polymerase, as in primer extension, RNA transcription, and/or the Polymerase Chain Reaction (PCR).

In some embodiments, the unique sequence comprise one or more sense or antisense sequences selected from, or readily converted to, the group of sequences (or portions thereof) consisting of transcription factor binding sites, binding sites for RNA binding proteins, binding sites for DNA binding proteins, binding sites for DNA polymerases, binding sites for DNA and/or RNA modifying enzymes including endo- and exonucleases, restriction endonucleases, ligases, integrases, recombinases, and topoisomerases, sequences known as polylinker regions, sequences known to encode genes or portions thereof including positive and negative selectable marker genes such as ampicillin resistance, kanamycin resistance, tetracycline resistance, Zeocin™ resistance (Zeocin is a registered trademark of Cayla), resistance to aminoglycoside antibiotics such as gentamycin and G418 (G418 is also known by the trademark Geneticin® registered to Life Technologies, Inc.), thymidine kinase, cholera toxin, diptheria toxin, suppressor tRNA genes (e.g. supf, sequences known to encode genes or portions thereof known as visible marker genes such as green fluorescent protein and variants, dsRed protein and variants, binding sites for RNA and DNA single-strand binding proteins, binding sites for proteins involved in strand invasion and recombination such as RecA, binding sites for DNA or RNA antibodies or putative auto-antigens such as Hu and La, binding sites for virally-encoded and/or bacteriophage-encoded DNA or RNA factors such as viral coat proteins and/or factors, envelop proteins and/or factors, packaging proteins and/or factors, sequences or portions thereof encoding regions implicated in phage, plasmid, cosmid, fosmid, artificial chromosome maintenance, immunity, and copy number control, binding sites for organic and/or inorganic molecules and/or cofactors and/or ions, such chemical compounds including therapeutic compounds, sequences known to perform catalytic activities such as ribozymes and autocatalytic self-splicing introns, sequences referred to as riboswitches or portions thereof, sequences known is internal ribosome entry sites (IRES), sequences known as untranslated or structural RNA molecules or portions thereof such as tRNA, 5S RNA, 7S RNA, ribosomal RNAs, X-inactivation RNAs (e.g. XIST), sequences known to be involved in RNA maintenance, transport, or degradation or portions thereof including 5' and 3' untranslated regions (UTRs), binding sites for factors involved in RNA maintenance, transport or degradation, sequences known as substrates for eukaryotic RNA capping enzymes, sequences known or predicted to act as interfering RNAs (RNAi) and/or double-stranded RNAs (dsRNA), sequences readily convertible into one or more micro RNAs (miRNAs) and or double-stranded RNAs (dsRNA), sequences and/or structures known or predicted to stimulate and/or recruit factors involved in dsRNA response and/or RNA interference (RNAi) response, structural binding sites for chromosomal attachment elements such as matrix attachment regions (MARs) and scaffold attachment regions (SARs), centromeric sequences, telomeric sequences, and unique sequences designed to be identifiable by chemical decomposition and/or mathematical algorithm.

The derivatized SLRNA molecule can be expressed in the cell, resulting in the spliced leader sequence encoded by the derivatized SLRNA molecule being trans-spliced onto an RNA molecule to be isolated. In some embodiments, the expressing is accomplished by operatively linking the derivatized SLRNA molecule to a nucleic acid sequence comprising a promoter that is capable of directing expression of the derivatized SLRNA molecule. Consistent with the instant method and as disclosed in greater detail herein, the choice of promoter depends only on the nature of the trans-spliced RNAs that one wishes to isolate. Thus, promoters include, but are not limited to constitutive, ubiquitous, cell-type-specific, tissue-specific, and inducible promoters. With regard to cell-type-specific and tissue-specific promoters, numerous such lineage-restricted promoters have been identified in *C. elegans*, and any of these promoters can be used in the methods of the presently disclosed subject matter. A list of over one hundred and eighty (180) such promoters can be found on the website of Professor Shawn Lockery at the University of Oregon. Numerous other tissue and cell type-specific promoters, both in *C. elegans* and in other species, have been identified in the scientific literature and can be employed in the methods of the presently disclosed subject matter.

In some embodiments, the derivatized SLRNA molecule is co-expressed with one or more other genes by operatively linking to a nucleic acid sequence comprising sequences encoding these genes. In some embodiments co-expression is accomplished by co-transformation. In some embodiments co-expression is achieved cloning derivatized SLRNA molecule together or separately with one or more other genes under the control of a common promoter. In some embodiments co-expression is accomplished by operatively linking the derivatized SLRNA molecule to other genes in an operon.

Trans-spliced RNAs comprising spliced leaders comprising unique sequences are detected and/or isolated using any of a variety of techniques. In some embodiments, RNA can be isolated from the cell, tissue, organ, or whole organism and reverse transcribed with reverse transcriptase using a poly-dT primer, random primers, or gene-specific primers, to prime first strand synthesis. After first-strand synthesis, second-strand synthesis can be accomplished using a primer that hybridizes to the unique sequence. The resulting population of double-stranded cDNAs corresponds to those RNA molecules to which a derivatized splice leader was trans-spliced. While the use of reverse transcription using a second-strand primer hybridizing to the unique sequence can be used to isolate trans-spliced RNAs comprising the spliced leader sequence comprising the unique sequence, any other method for isolating these molecules can be employed.

In some embodiments, isolation of trans-spliced RNAs comprising spliced leaders comprising unique sequences can be accomplished using sequence specific hybridization between the unique sequence and other sequences. In some embodiments trans-spliced RNAs can be amplified and/or isolated using the Polymerase Chain Reaction (PCR), using all or portions of the unique sequence as a primer hybridization (binding) site. In some embodiments molecular recognition is employed exclusive of, or in addition to, sequence specific hybridization to unique sequences. In some embodiments nucleotide sequences comprise chemically modified nucleotides and nucleosides, including but not limited to dUTP, dITP, PNA-coupled nucleotides, phosphorothioate nucleotides, amino-allyl nucleotides, terminally or internally modified nucleotides including amino-, thio-, and vicinal diol-modified nucleotides. In some embodiments nucleotide sequences are covalently attached to other molecules such as biotin, glutathione, digoxigenin or other steroidal compounds, chelation agents such as EDTA, EGTA, and DTPA, fluorescent reporter molecules, or haptens. In some embodiments nucleotide sequences are covalently attached to polypeptides or proteinaceous molecules. In some embodiments sequences are covalently attached to carbohydrate molecules or lipids, or therapeutic agents, or cellular cofactors. In some embodiments sequences are modified and/or recognized using crosslinking, intercalation, and/or chemical cleavage agents and mutagens. In some embodiments sequences are modified using compounds known as infrared labels, spin labels, Mossbauer labels, excimers, fluorescent molecules, phosphorescent molecules, or groups of such molecules to accomplish fluorescence resonance energy transfer (FRET). In some embodiments sequences are recognized by non-covalent interactions including antibody binding, host-guest interactions, and molecular intercalation. In some embodiments sequences are covalently or non-covalently attached to surfaces on capillaries, beads, or other solid supports and matrices. In some embodiments sequences are arrayed on solid supports.

In some embodiments sequences are detected and/or isolated using one or more of the following techniques: optical measurement, differential hybridization, differential precipitation, differential crystallization, electrophoresis including capillary electrophoresis, column chromatography, hydroxyapatite chromatography, streptavidin binding, laser-induced fluorescence, flow cytometry cell sorting (FACS), fluorescence correlation spectroscopy, surface plasmon resonance, atomic absorption, nuclear magnetic resonance (NMR), or mass spectroscopy.

These strategies can also be employed to isolate a plurality of RNA molecules expressed in cells of interest, which can then be used to produce libraries of trans-spliced RNA molecules. In some embodiments, libraries of trans-spliced molecules can be identified, modified, isolated, separated, sorted, and arrayed, by the methods disclosed herein, or by other methods.

In some embodiments, one, many, or the plurality of genes and/or gene products identified using derivatized trans-spliced SLRNA molecules are used to generate recombinant RNA molecules and/or polypeptides. In some embodiments said RNA molecules and/or polypeptides are arrayed on solid support. In some embodiments, materials described herein are assembled as one or more reagents in kits for producing the desired embodiment, as described herein.

In some embodiments, one, many, or the plurality of genes and/or gene products identified using derivatized trans-spliced SLRNA molecules are tested and/or used to generate and/or isolate a cell, tissue, organ, or organism with a desired phenotype.

In some embodiments, the methods disclosed herein are employed in functional analysis of genes and gene products wherein one, many, or a plurality of expressed genetic sequences and/or gene products are used to restore normal function to a cell, tissue, or organism by means of trans-genesis and/or transformation, such methods being generally referred to as complementation, and/or to obliterate functionality in a cell, tissue, or organism, such method being generally referred to as knock-out, loss-of-function or hypomorphic analysis, and/or to increase endogenous functionality in a cell, tissue, or organism, such method being generally referred to as over-expression, gain-of-function or hypermorphic analysis, and/or to introduce novel functionality in a cell, tissue, or organism, such method being generally referred to as heterologous expression, chimeragenesis, and/or neomorphic analysis. In some embodiments trans-genesis and/or transformation can be employed in a number of functional strategies whereby complementation activity, loss-of-function activity, gain-of-function activity, or novel activity can be absolutely ascribed to the presence of one or more gene sequences and/or gene products. Functional strategies include the one or more of the group of strategies known as selection, screening, and sib-selection; sib-selection is generally described as the iterative procedure whereby simpler and simpler pools of gene sequences and/or gene products are introduced to produce a desired cellular, tissue-specific, or organismal effect until pools can no longer be simplified without loss of functional activity, often resulting in the identification of a single, functional molecular species. Trans-genic and/or transformation strategies may additionally comprise use of gene and/or gene products as co-transformation markers. Transgenic and/or transformation strategies can be employed to implicate one or more indirect or direct mechanisms: indirect mechanisms include mechanisms generally known as epistatic and/or bypass suppression and/or activation, while direct mechanisms imply physical interaction between exogenously added gene or gene products and endogenous cellular, tissue-specific, and/or organismal constituents. Direct mechanisms include mechanisms generally known as dominant-negative interaction and dominant-positive interaction.

In some embodiments, the methods described herein are used to determine if two or more genes are co-expressed in the same cell. In some embodiments, the methods described herein are used to simultaneously compare levels of gene expression in two or more different cells, tissues, and/or organs. In some embodiments, the methods described herein are used to determine if two or more cells, tissues, and/or organs express identical or near identical sets of genes. In some embodiments the methods described herein are used to determine if two or more cells, tissues, and/or organs express overlapping sets of genes. In some embodiments the methods described herein are used to determine if two or more cells, tissues, and/or organs express distinct sets of genes. In some embodiments the methods described herein are used to estimate and/or determine the number of cell types present within tissues, organs, and/or organisms.

In some embodiments the methods described herein are used to determine cell type specific expression in organisms with defined genetic mutations. In some embodiments the methods described herein are used to determine cell type specific expression in organisms in response to environmental factors and/or chemical exposure.

In some embodiments the methods described herein are used to detect cell type specific expression during individual behaviors such as chemosensation, thermosensation, mechanosensation, lights sensation, auditory sensation, molting, parturition, and defecation. In some embodiments the methods described herein are used to detect cell type specific expression during social behavior of an organism species, including feeding and mating. In some embodiments the methods described herein are used to detect cell type specific expression in a species of organism existing in the presence of or symbiotically with one or more other organism species. In some embodiments the methods described herein are used to detect cell type specific expression in a species of organism infecting or being infected by one or more other organism species. In some embodiments the methods described herein are used to detect cell type specific expression in a species of organism parasitizing or being parasitized one or more other organism species.

V. Organisms

The methods of the presently disclosed subject matter can be used to isolate trans-spliced RNAs from any organism that normally trans-splices spliced leaders onto RNAs. Such organisms include, but are not limited to cnidarians, ascidians, nematodes, trematodes, cestodes, and helminthes. Representative organisms include *C. elegans, Schistosoma* sp., soil-transmitted helminthes, *Onchocerca volvulus, Brugia malayi, Heterorhabditis bactediophora, Haemonchus contortus,* and *Wucheria bancrofti.*

The methods of the presently disclosed subject matter can also be used to isolate designed spliced leader (Tagon) trans-spliced RNAs from any multicellular organism that performs spliceosome-mediated cis-splicing RNAs. Transfection of nematode and trypanosomal spliced leader sequences into mammalian cells has been shown to direct SL-addition trans-splicing to model acceptor substrates with minimal sequence-specific informational content (Bruzik and Maniatis 1992). Experimental results indicate cis- and trans-splicing are in a simple molar-based competition (Conrad, Liou et al. 1993; Conrad, Lea et al. 1995). Therefore Tagon addition to individual mRNAs would be expected to successfully compete with ("subvert") cis-splicing to cause SL-addition at a detectable level at a location within normally cis-spliced genes. Rapid SL-induction and/or gene isolation allows recovery of subsets of genes from complex tissue. Such organisms include, but are not limited to mammalian, avian, reptile, and amphibian lineages. Representative organisms include *Homo sapiens, Bos Taurus, Rattus norveticus, Mus musculus, Xenopus laevis, Dania rerio*, Invertebrate organisms for which SL-addition trans-splicing is not known, but for which Tagon-cloning may prove useful include *Drosophila melanogaster.*

Representative multicellular organisms that perform spliceosome-mediated cis-splicing can be warm-blooded vertebrates, for instance, mammals and birds. In some embodiments, the animal is selected from the group consisting of rodent, swine, bird, ruminant, and primate. In some embodiments, the animal is selected from the group consisting of a mouse, a rat, a pig, a guinea pig, poultry, an emu, an ostrich, a goat, a cow, a sheep, and a rabbit. In some embodiments, the animal is a primate, such as an ape, a monkey, a lemur, a tarsier, a marmoset, or a human.

Thus, provided is the treatment of mammals such as humans, as well as those mammals of importance due to being endangered (such as Siberian tigers), of economic importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the treatment of birds, including the treatment of those kinds of birds that are endangered, kept in zoos, as well as fowl, and more particularly domesticated fowl, e.g., poultry, such as turkeys, chickens, ducks, geese, guinea fowl, and the like, as they are also of economic importance to humans. Thus, provided is the treatment of livestock, including, but not limited to, domesticated swine (pigs and hogs), ruminants, horses, poultry, and the like.

EXAMPLES

The following Examples provide illustrative embodiments of the presently disclosed subject matter. In light of the present disclosure and the general level of skill in the art, those of skill will appreciate that the following Examples are intended to be exemplary only and that numerous changes, modifications, and alterations can be employed without departing from the scope of the presently disclosed subject matter.

Experimental Procedures

Figure 3:
FIGS. 3A-3D schematically depict a strategy for the isolation of two distinct populations of cDNA from *C. elegans* without dissection using a neural-specific promoter and a gut-specific promoter.
Figure 3:
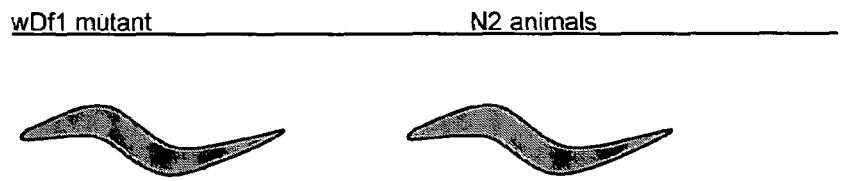
Figure 3:
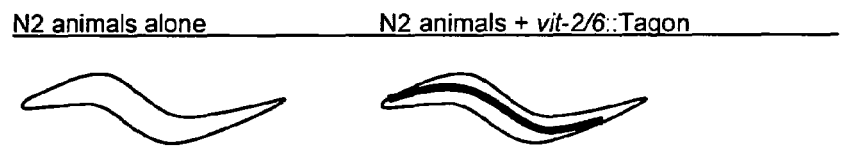
Figure 3:
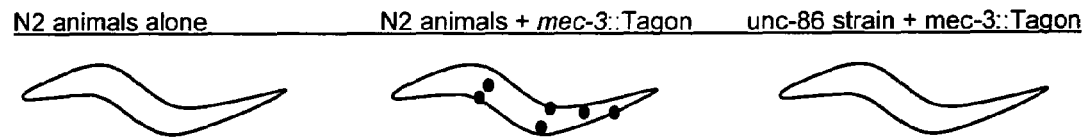

Tagon cloning is shown by:

1. Complementing SL RNA-deficient mutant animals with mutated (Tagon) SL RNAs;

2. Determining the extent to which sequences can be altered and/or inserted within or adjacent to the SL mini-exon; and 3. Demonstrating that two distinct populations of cDNA can be obtained from C. elegans without dissection using a neural-specific promoter and a gut-specific promoter. A diagram of animals and expected recovery of mRNA is shown in FIG. 3.

Table 1 outlines an approach that can be used to recover genes using the Tagon method, in comparison to standard cDNA cloning methods using 5' RACE. WDf1 is a C. elegans strain deleted for the SLRNA cluster. Cloning using oligo-dT and a linker ligated to the 5' end recovers all genes expressed in the animal. Cloning using a SL primer should not recover any genes because SL-trans-splicing is absent. The normal situation is shown in the standard N2 strain, which allows recovery of all genes using a 5' linker primer and a 3' oligo-dT primer, and allows recovery of all SL1 trans-spliced genes using a 5' SL1 primer.

In gut, the genes ges-1 and elt-2 demonstrate tagging of gut-specific genes, since these genes are expressed in gut tissue. In touch neurons, the genes mec-3 and alpha-2 tubulin demonstrate tagging of touch neuron-specific genes, since these genes are expressed in touch neurons. Elt-2 and ges-1 expression in touch neurons is absent, as is mec-3 and alpha-2 tubulin expression in gut tissue.

Use of Tagon constructs in a modified genetic background demonstrates specificity of Tagon method. Touch neurons fail to differentiate properly in Unc-86 mutant animals. In Unc-86 animals transformed with Tagon constructs, mec-3 and alpha-2 tubulin gene expression is turned off. PCR analysis of tagged genes demonstrates this change in mec-3 and alpha-2 tubulin expression. This analysis demonstrates the exquisite sensitivity of the technique, because touch neurons comprise only six cells of the C. elegans organism.

TABLE 1 mRNA Recovery for Above Strains Using Defined PCR Primers

| Strain | 5'-primer | 3'-primer | mRNA recovered |
|---|---|---|---|
| A. wDf1 | 1. linker adaptor | oligo-dT | all genes |
|  | 2. SL-oligo | oligo-dT | 0 genes |
| A. N2 | 1. linker adaptor | oligo-dT | all genes |
|  | 2. SL1-oligo | oligo-dT | SL1-spliced genes |
| B. wDf1 U2-3::Tagon | 1. linker adaptor | oligo-dT | all genes |
|  | 2. SL-oligo | oligo-dT | 0 genes |
|  | 3. Tagon-oligo | oligo-dT | Tagon-spliced genes |
| B. N2 U2-3::Tagon | 1. linker adaptor | oligo-dT | all genes |
|  | 2. SL1-oligo | oligo-dT | SL1-spliced genes |
|  | 3. Tagon-oligo | oligo-dT | Tagon-spliced genes |
| C. N2 vit-2/6::Tagon | 1. linker adaptor | oligo-dT | all genes |
|  | 2. SL1-oligo | oligo-dT | SL1-spliced genes |
|  | 3. Tagon-oligo | a. oligo-dT | Tagon-spliced genes (only in the gut) |
|  | 3. Tagon-oligo | b. ges-1 oligo | ges-1 gut expression |
|  | 3. Tagon-oligo | c. elt-2 oligo | elt-2 gut expression |
| D. N2 mec-3::Tagon | 1. linker adaptor | oligo-dT | all genes |
|  | 2. SL1-oligo | oligo-dT | SL1-spliced genes |
|  | 3. Tagon-oligo | oligo-dT | Tagon-spliced genes (only in touch cells) |
|  | 3. Tagon-oligo | mec-3 oligo | touch cell mec-3 level (expression is ON). |
|  | 3. Tagon-oligo | a-2 tubulin | touch cell a-2 level (expression is ON) |
| D. Unc-86 mec-3::Tagon | 1. linker adaptor | oligo-dT | all genes |
|  | 2. SL1-oligo | oligo-dT | SL1-spliced genes |
|  | 3. Tagon-oligo | oligo-dT | Tagon-spliced genes (only in touch cells) |
|  | 3. Tagon-oligo | mec-3 oligo | touch cell mec-3 level (expression is OFF) |
|  | 3. Tagon-oligo | a-2 tubulin | touch cell a-2 level (expression is OFF) |

Transgenic animals containing altered (Tagon) SLRNA genes allow recovery of specific populations of genes. Under the control of the U2-3 promoter Tagon is expressed ubiquitously. When Tagon is expressed in either wDf1 strain or N2 strain under a ubiquitous promoter, all SL1 trans-spliced genes are recovered (referred to herein as "Tagon-spliced" genes).

When expressed under two different tissue-specific promoters, Tagon permits the recovery of different populations of cells. Under the control of the vit-2/6 promoter, Tagon expression is confined to gut tissue. Under the control of the mec-3 promoter, Tagon expression is confined to mechanosensory (touch) neurons. Table 1 indicates that these populations are recoverable by use of the correct primer pair.

SL Mutagenesis

C. elegans clones are obtained from the Gene Sequencing Consortium. Approximately 60% of genes in C. elegans are trans-spliced to SL1, the first C. elegans spliced leader gene discovered (Blumenthal 1995). The SL1 RNA gene will be modified so that it encodes a "Tagon" sequence at its 5'-end within or adjacent to the spliced leader "mini-exon".

Four constructs are made where individual nucleotides are replaced within the SL sequence to produce a novel Tagon sequence (FIG. 2). Four constructs are made where Tagon sequences are added 5' of the SL sequence, and four constructs are made where Tagon sequences are added 3' of the SL sequence. All synthetic sequences are long enough (16-20 nucleotides) to allow PCR amplification. Tagon sequences are checked against *C. elegans* genomic sequences to prevent inadvertently matching genomic sequences. Tagon sequences do not resemble other spliced leader sequences in *C. elegans*, since previous experiments have shown that such chimeric constructs are not utilized (Ferguson and Rothman 1999). Mutagenesis is performed on the DNA using standard in vitro techniques (oligonucleotide-mediated, PCR-mediated, etc.). Tagon expression is assumed to be co-dominant in wild type animals.

Promoter Fusion and Analysis

The SL1 RNA has an internal DNA transcriptional promoter element that corresponds to the spliced leader sequence. The presence of an internal promoter (and initiator element) within the SL RNA might help explain the remarkable conservation of this 22-nucleotide sequence throughout the nematode phylogeny (Maroney, Hannon et al. 1990). The endogenous promoter sequence can be mutated or removed to prevent inappropriate expression in all cells of the animal. If this sequence is mutated dramatically (as in the creation of a Tagon sequence) the endogenous promoter is thus mutated and expression from the endogenous promoter is obliterated (Xie and Hirsh 1998). There is also an upstream element called a Proximal Sequence Element (PSE). This element is at a defined distance approximately 60 basepairs 5' of the initiation of transcription, as defined in the related nematode *Ascaris suum* (Maroney, Hannon et al. 1990).

a. To test for rescuing ability of the Tagon sequences, the 12 synthetic constructs are sub-cloned downstream of the U2-3 promoter, used successfully in previous studies to drive SL RNA expression (Ferguson and Rothman 1999). To obliterate expression from the endogenous SLRNA promoter, the Proximal Sequence Element (PSE) is removed from all 12 constructs.

b. *C. elegans* strains are obtained from the CGC, the *C. elegans* Genetic Stock Center. DNA is introduced into the wDf1 strain, a deletion strain missing the rrs-1 cluster, an array of SL1 RNA/5S RNA genes (Nelson and Honda 1989; Ferguson, Heid et al. 1996). *C. elegans* animals are transformed by standard microinjection techniques, and progeny recovered. Homozygous wDf1 animals normally die during embryogenesis due to a deficiency of the SL RNA gene product. Microinjected DNA in *C. elegans* forms extrachromosomal arrays that can express genes at high levels. This technique is used to determine which of the 12 Tagon sequences are capable of rescuing embryonic lethality. Rescuing lines are analyzed by established methods (Ferguson and Rothman 1999).

c. Rescuing Tagon-SLRNA constructs without the U2-3 promoter are injected into the rrs-1 strain of *C. elegans* animals by standard microinjection techniques as a control experiment. These "promoter-less" constructs can show that rescue of embryonic lethality is dependent upon the presence of the U2-3 promoter, and not on any residual expression from the original SL RNA promoter or internal promoter elements.

d. U2-3 dependent rescuing Tagon-SLRNA constructs are chosen for further analysis based on their original design class (5', internal, or 3'). For example, if insertions 5' of the spliced leader are the most effective class at rescuing wDf1 embryonic lethality, then Tagon-SLRNAs of this class are exclusively used in further studies.

e. Tagon sequences can potentially interact negatively with other cellular products in wild-type animals. To determine if Tagon SL sequences are 'toxic' to the animal, rescuing synthetic U2-3:: tagon-SLRNA constructs are microinjected into wild-type N2 *C. elegans* animals and transformed progeny recovered. Normal animal behavior, lifespan, and fecundity are assayed and compared to uninjected N2 animals. Splicing of Tagon sequences onto mRNAs is confirmed by RT-PCR using conserved 3' gene-specific primers. Candidate gene-specific primers include act-1 and myo-3 genes, both of which are known to be trans-spliced to SL1.

f. To confirm that multiple different Tagon sequences can be utilized in SL-addition trans-splicing, oligo-directed mutagenesis using random mutagenic oligonucleotides is used to create a 'pool' of SL RNA genes with a twenty base-pair random block insertion. This pool is cloned en masse downstream of the U2-3 promoter. Pooled clones are microinjected into N2 animals, transgenic lines established, and progeny analyzed. RNA is isolated and direct DNA sequencing is performed using a gene-specific primer for a ubiquitously expressed gene (for example, act-1), Reverse Transcriptase, and an RNA template. A heterogeneous series of DNA sequencing peaks at the 5' end of the mRNA indicates that trans-splicing can tolerate multiple different base changes within or adjacent to the SL mini-exon.

g. Tissue-specific expression is tested in the *C. elegans* gut by cloning a Tagon-SLRNA gene downstream of the vitellogenin promoter vit-2/vit-6 (MacMorris, Spieth et al. 1994). The vit-2/vit-6:: Tagon-SLRNA construct is expressed only in the animal's intestine. To confirm that gut-specific genes can be recovered by this method, primers are designed for the ges-1 and elt-2 genes, both gut-specific genes normally trans-spliced to SL1 (Kennedy, Aamodt et al. 1993; Hawkins and McGhee 1995). These two genes are amplified by RT-PCR using a Tagon primer to amplify mRNA transcripts spliced to the Tagon sequence. Positive PCR bands of the correct length is sequenced to confirm gene sequence and proper trans-splicing.

h. Determination of cell-type specific expression. *C. elegans* has approximately 3000 nuclei in adult animals but only six touch receptor neurons. mec-3 is a transcription factor required for differentiation of these six touch receptor neurons in *C. elegans*. This promoter is used for the selective amplification of genes expressed in only eight cells, the six touch receptor cells and the neurons FLP and PVD (Way and Chalfie 1989).

Cell-type specific Tagon expression is driven from the mec-3 promoter. A short 71-bp mec-3 regulatory element added to a minimal promoter is sufficient to recapitulate the mec-3 expression pattern (Way and Chalfie 1989). A non-toxic rescuing Tagon construct is sub-cloned downstream of this mec-3 promoter. Transgenic lines are established in N2 (wild-type) and unc-86 mutant backgrounds. unc-86 animals are mechanosensory-defective because they have cell lineage defects that disrupt touch cell receptor neurons (Chalfie, Horvitz et al. 1981).

RNA is isolated from each line. RT-PCR is performed using two gene-specific primers: mec-9 and alpha-2 tubulin, both of which are known to trans-splice SL1 (Fukushige, Yasuda et al. 1993; Du, Gu et al. 1996). PCR products are seen in wild type N2 lines and abolished in unc-86 lines. Positive PCR bands of the correct length are sequenced to confirm gene sequence and proper trans-splicing.

i. Control experiments are performed in both vit-2/vit-6:: Tagon and mec-3::Tagon strains. RT-PCR should fail to amplify touch receptor neuron genes mec-9 and alpha-2 tubulin in strains expressing Tagon-SLRNA only in gut (vit-2/vit-6:: Tagon). RT-PCR should fail to amplify gut-specific genes ges-1 and elt-2 in strains expressing Tagon-SLRNA only in the touch receptor neurons (mec-3:: Tagon).

Multiplexed Tagon

In some embodiments and unlike other techniques (e.g., mRNA tagging), Tagon cloning allows the simultaneous or "multiplexed" purification of cDNA from multiple tissues by RT-PCR. Organisms can be transformed with multiple Tagon-SLRNA genes (Tagon1-SLRNA, Tagon2-SLRNA, etc.), each being expressed under a different promoter. First strand cDNA synthesis is primed by an oligo-dT primer as usual, and then the template is separated into different reactions. A unique Tagon primer is added to each reaction, (Tagon1, Tagon2, Tagon3, etc.), and second strand cDNA synthesis is carried out. Dozens of cell groups (e.g., sensory neurons, interneurons, motor neurons, etc.) can be monitored independently and simultaneously (Table 2). Genome wide expression can be analyzed on microarrays or by SAGE. Alternatively, individual gene expression levels can be monitored using real-time PCR, e.g. by Taqman™ analysis, using a Tagon primer to give tissue-specific semi-quantitative levels of gene expression based on real time PCR.

TABLE 2

Primer Sets and Predicted Gene Recovery

| 5'Primer | 3'Primer | Genes Recovered |
|---|---|---|
| ligate linker | oligo-dT | all genes |
| SL1 primer | oligo-dT | all SL1 trans-spliced genes |
| Tagon1 primer | oligo-dT | all trans-spliced genes in Tagon1 expressing cells |
| Tagon2 primer | oligo-dT | all trans-spliced genes in Tagon2 expressing cells |
| Tagon1 primer | gene A | test if trans-spliced gene A is co-expressed with Tagon1 |
| Tagon2 primer | gene A | test if trans-spliced gene A is co-expressed with Tagon2 |

In some embodiments, co-expression of two trans-spliced genes can be rapidly tested. This "co-expression" test can be used, for example, to determine if interactions predicted using the yeast "two-hybrid" system can actually occur in vivo in the natural organism; i.e., to determine whether the two putative interacting polypeptides are co-expressed in the same cells at the same time. This experiment can be carried out routinely by researchers without access to microarrays.

Briefly, Tagon1 is cloned downstream of gene A's promoter, and Tagon2 is cloned downstream of gene B's promoter. These constructs are co-injected together and a transgenic line is established. To determine co-expression, RT-PCR is performed. Positive PCR bands are expected (by definition) for Tagon1/gene A and Tagon2/gene B. However, positive PCR bands for Tagon1/gene B and Tagon2/gene A indicate that each gene is expressed in cells in which the other gene's promoter is active (Table 3).

This technique could be used to determine co-expression even in genes that are only cis-spliced. In C. elegans, cis-spliced genes can be converted into trans-spliced genes by removal of the 5'-most splice site.

TABLE 3

Co-expression Test

| Promoter | Tagon No. | RT-PCR Gene A | RT-PCR Gene B |
|---|---|---|---|
| Gene A | Tagon 1 | (+) control | if (+), then co-expressed |
| Gene B | Tagon 2 | if (+), then co-expressed | (+) control |

In some embodiments, sets of co expressed and non co-expressed genes are defined. The experiments above show an identity property as expected: if gene X is expressed in gene Y expressing cells, then gene Y is expressed in gene X-expressing cells. However, if [A and B] are co-expressed and [B and C] are co-expressed, there is no guarantee that [A and C] are co-expressed. Venn diagrams of expression can thus be defined, and new sets can be derived using experiments that fail to show reciprocal products, such as the set [A not B], and the set [C not B].

For example, gene B could be expressed in both neurons and gut, gene A could be neuron specific, and gene C could be gut specific. A co-expression test of [A and C] would fail to show reciprocal products. Increasingly precise sets of genes can be defined, such as the set [promoter A not promoters C, D, E] and [promoter C not promoters A, D, E].

In some embodiments tests are performed to estimate the extent of gene expression and patterns of overlapping expression. In the classic probability problem, two persons in a small group of people can be shown to have a high probability of having the same birthday. The same method of random sampling can be used to estimate number of cell types and/or overlapping fields of gene expression. Using C. elegans as a model system, as a worse case scenario assume that each gene is only expressed in one somatic cell. Using the total number of somatic cells as a starting point (959) and assuming that all genes are expressed somatically, the probability that all genes are expressed in different cells is given by the equation:

$$Pr(E) = (959 - n + 1)/959^n$$

Thus assuming that each gene is expressed in only one cell, the probabilities that any two genes will be co-expressed in the same cells is actually quite high [$Pr(E') = 1 - Pr(E)$]

TABLE 4

Binary Expression Test

| | n Promoters | | | | |
|---|---|---|---|---|---|
| | 4 | 8 | 12 | 16 | 20 |
| | Strains(n pair) | | | | |
| | 6 | 28 | 66 | 120 | 190 |
| | Gene-specific studies | | | | |
| reciprocal PCRs | 12 | 56 | 132 | 240 | 380 |
| | Worst case (one gene per cell) | | | | |
| uniquely expressed | 99.4% | 97.1% | 93.3% | 88.2% | 81.9% |
| overlapping | 0.6% | 2.9% | 6.7% | 11.8% | 18.1% |
| | Each gene in 6 cells: | | | | |
| uniquely expressed | 96.3% | 83.7% | 65.5% | 46.0% | 29.0% |
| overlapping | 3.7% | 16.3% | 34.5% | 54.0% | 71.0% |
| | Libraries | | | | |
| Individual pools | 6 | 28 | 66 | 120 | 190 |
| Tagon libraries | 12 | 56 | 132 | 240 | 380 |
| total binary sets | 264 | 6160 | 3.5E4 | 1.1E5 | 2.9E5 |

Figure Legend. Probability that two randomly selected genes each expressed in the minimum number of cells (1 cell each) are found to be co-expressed in the same cell, for n genes. Individual genes are described under study in top sections of table, libraries are described under study in bottom section, for use in microarray and/or SAGE analysis. "Total binary sets" defined as combination of libraries C(n,r) times 4 (the sets [A not B], [B not A], [A or B], [A and B]).

If all genes are expressed in six cells each, then there is actually a greater than 50% chance that two genes will be co-expressed when 16 or more genes are studied. Under the worse case scenario that each gene is only expressed in one cell, there is an approximately 25% chance that any two genes will be co-expressed for 24 genes.

Extension of this methodology, in *C. elegans* and other organisms, studying multiple gene expressed in individual cells, and utilizing microarray analysis and/or SAGE analysis, promises to rapidly identify individual cells belonging to a common cell type, similar and distinct cell types based on overlapping and mutually-exclusive sets of expressed genes, and estimates of absolute number of cell types in tissues, organs, and whole organisms.

What defines cell type? How can these definitions be improved by novel techniques? Generally stated, the morphological, enzymatic and antigenic properties of a particular cell type are defined by the expression of large and varied sets of genes in any one particular cell type. The extensive adoption of GFP technology by research communities has shifted the focus of cell type identification from antigenic and histological techniques to a molecular technique. The adoption of a more comprehensive technology as described herein will hopefully shift the focus of cell type identification from the present operative definition using promoter::GFP constructs, to clusters of hundreds or even thousands of genes that are co-expressed in the same cells at the same time. Once adequately identified, cell types can be monitored for appropriate or inappropriate changes in gene expression during mutation, infection, disease progression, drug development, and toxicology testing.

REFERENCES

The references listed below as well as all references cited in the specification are incorporated herein by reference to the extent that they supplement, explain, provide a background for, or teach methodology, techniques, and/or compositions employed herein.

Amatschek, S., U. Koenig, et al. (2004). "Tissue-wide expression profiling using cDNA subtraction and microarrays to identify tumor-specific genes." *Cancer Res* 64(3): 844-56.

Andrews, J., G. G. Bouffard, et al. (2000). "Gene discovery using computational and microarray analysis of transcription in the *Drosophila melanogaster* testis." *Genome Res* 10(12): 2030-43.

Bard, E. (1989). "Molecular biology of *Leishmania*." *Biochem Cell Biol* 67(9): 516-24.

Bektesh, S., K. Van Doren, et al. (1988). "Presence of the *Caenorhabditis elegans* spliced leader on different mRNAs and in different genera of nematodes." *Genes Dev* 2(10): 1277-83.

Bektesh, S. L. and D. I. Hirsh (1988). "*C. elegans* mRNAs acquire a spliced leader through a trans-splicing mechanism." *Nucleic Acids Res* 16(12): 5692.

Blumenthal, T. (1995). "Trans-splicing and polycistronic transcription in *Caenorhabditis elegans*." *Trends Genet* 11(4): 132-6.

Bruzik, J. P. and T. Maniatis (1992). "Spliced leader RNAs from lower eukaryotes are trans-spliced in mammalian cells." *Nature* 360(6405): 692-5.

Chabardes-Garonne, D., A. Mejean, et al. (2003). "A panoramic view of gene expression in the human kidney." *Proc Natl Acad Sci USA* 100(23): 13710-5.

Chalfie, M., H. R. Horvitz, et al. (1981). "Mutations that lead to reiterations in the cell lineages of *C. elegans*." *Cell* 24(1): 59-69.

Chin, K. and A. M. Pyle (1995). "Branch-point attack in group II introns is a highly reversible transesterification, providing a potential proofreading mechanism for 5'-splice site selection." *Rna* 1(4): 391-406.

Conrad, R., K. Lea, et al. (1995). "SL1 trans-splicing specified by AU-rich synthetic RNA inserted at the 5' end of *Caenorhabditis elegans* pre-mRNA." *Rna* 1(2): 164-70.

Conrad, R., R. F. Liou, et al. (1993). "Conversion of a trans-spliced *C. elegans* gene into a conventional gene by introduction of a splice donor site." *Embo J* 12(3): 1249-55.

Conrad, R., J. Thomas, et al. (1991). "Insertion of part of an intron into the 5' untranslated region of a *Caenorhabditis elegans* gene converts it into a trans-spliced gene." *Mol Cell Biol* 11(4): 1921-6.

Cras-Meneur, C., H. Inoue, et al. (2004). "An expression profile of human pancreatic islet mRNAs by Serial Analysis of Gene Expression (SAGE)." *Diabetologia* 47(2): 284-99.

Cressman, C. P. and P. L. Williams (1997). Reference toxicants for toxicity testing using *Caenorhabditis elegans* in aquatic media. Environmental Toxicology and Risk Assessment: Modeling and Risk Assessment. F. J. Dwyer, T. R. Doane and M. L. Hinman, American Society for Testing and Materials. 1317:6: 518-532.

Custodia, N., S. J. Won, et al. (2001). "*Caenorhabditis elegans* as an environmental monitor using DNA microarray analysis." *Ann NY Acad Sci* 948: 32-42.

Da'Dara, A. A., K. Henkle-Duhrsen, et al. (1996). "A novel trans-spliced mRNA from *Onchocerca volvulus* encodes a functional S-adenosylmethionine decarboxylase." *Biochem J* 320 (Pt 2): 519-30.

Davis, R. E. (1997). "Surprising diversity and distribution of spliced leader RNAs in flatworms." *Mol Biochem Parasitol* 87(1): 29-48.

Davis, R. E., C. Hardwick, et al. (1995). "RNA trans-splicing in flatworms. Analysis of trans-spliced mRNAs and genes in the human parasite, *Schistosoma mansoni*." *J Biol Chem* 270(37): 21813-9.

Donkin, S. G. and D. B. Dusenbery (1993). "A soil toxicity test using the nematode *Caenorhabditis elegans* and an effective method of recovery." *Archives of Environmental Contamination and Toxicology* 25: 145-151.

Du, H., G. Gu, et al. (1996). "Extracellular proteins needed for *C. elegans* mechanosensation." *Neuron* 16(1): 183-94.

Ferguson, K. C., P. J. Heid, et al. (1996). "The SL1 trans-spliced leader RNA performs an essential embryonic function in *Caenorhabditis elegans* that can also be supplied by SL2 RNA." *Genes Dev* 10(12): 1543-56.

Ferguson, K. C. and J. H. Rothman (1999). "Alterations in the conserved SL1 trans-spliced leader of *Caenorhabditis elegans* demonstrate flexibility in length and sequence requirements in vivo." *Mol Cell Biol* 19(3): 1892-900.

Fukushige, T., H. Yasuda, et al. (1993). "Molecular cloning and developmental expression of the alpha-2 tubulin gene of *Caenorhabditis elegans*." *J Mol Biol* 234(4): 1290-300.

Goeddel, D. V. (1990). "Systems for heterologous gene expression." *Methods Enzymol* 185: 3-7.

Goncharov, I., Y. X. Xu, et al. (1998). "Structure-function analysis of the trypanosomatid spliced leader RNA." *Nucleic Acids Res* 26(9): 2200-7.

Gorman, J. R., N. van der Stoep, et al. (1996). "The Ig(kappa) enhancer influences the ratio of Ig(kappa) versus Ig(lambda) B lymphocytes." *Immunity* 5(3): 241-52.

Halgren, R. G., M. R. Fielden, et al. (2001). "Assessment of clone identity and sequence fidelity for 1189 IMAGE cDNA clones." *Nucleic Acids Res* 29(2): 582-8.

Hannon, G. J., P. A. Maroney, et al. (1990). "Trans splicing of nematode pre-messenger RNA in vitro." *Cell* 61(7): 1247-55.

Harris, K. A., Jr., D. M. Crothers, et al. (1995). "In vivo structural analysis of spliced leader RNAs in *Trypanosoma brucei* and *Leptomonas collosoma*: a flexible structure that is independent of cap4 methylations." *Rna* 1(4): 351-62.

Hawkins, M. G. and J. D. McGhee (1995). "elt-2, a second GATA factor from the nematode *Caenorhabditis elegans*." *J Biol Chem* 270(24): 14666-71.

Kaestner, K. H., C. S. Lee, et al. (2003). "Transcriptional program of the endocrine pancreas in mice and humans." *Diabetes* 52(7): 1604-10.

Kennedy, B. P., E. J. Aamodt, et al. (1993). "The gut esterase gene (ges-1) from the nematodes *Caenorhabditis elegans* and *Caenorhabditis briggsae*." *J Mol Biol* 229(4): 890-908.

Konarska, M. M., R. A. Padgett, et al. (1985). "Trans splicing of mRNA precursors in vitro." *Cell* 42(1): 165-71.

Krause, M. and D. Hirsh (1987). "A trans-spliced leader sequence on actin mRNA in *C. elegans*." *Cell* 49(6): 753-61.

Liou, R. F. and T. Blumenthal (1990). "trans-spliced *Caenorhabditis elegans* mRNAs retain trimethylguanosine caps." *Mol Cell Biol* 10(4): 1764-8.

MacMorris, M., J. Spieth, et al. (1994). "Analysis of the VPE sequences in the *Caenorhabditis elegans* vit-2 promoter with extrachromosomal tandem array-containing transgenic strains." *Mol Cell Biol* 14(1): 484-91.

Maroney, P. A., G. J. Hannon, et al. (1990). "Transcription and cap trimethylation of a nematode spliced leader RNA in a cell-free system." *Proc Natl Acad Sci USA* 87(2): 709-13.

Maroney, P. A., G. J. Hannon, et al. (1991). "Intramolecular base pairing between the nematode spliced leader and its 5' splice site is not essential for trans-splicing in vitro." *Embo J* 10(12): 3869-75.

Mello, C. and A. Fire (1995). "DNA transformation." *Methods Cell Biol* 48: 451-82.

Mello, C. C., J. M. Kramer, et al. (1991). "Efficient gene transfer in *C.elegans*: extrachromosomal maintenance and integration of transforming sequences." *Embo J* 10(12): 3959-70.

Michaeli, S., T. G. Roberts, et al. (1990). "Isolation of distinct small ribonucleoprotein particles containing the spliced leader and U2 RNAs of *Trypanosoma brucei*." *J Biol Chem* 265(18): 10582-8.

Michels, W. J., Jr. and A. M. Pyle (1995). "Conversion of a group II intron into a new multiple-turnover ribozyme that selectively cleaves oligonucleotides: elucidation of reaction mechanism and structure/function relationships." *Biochemistry* 34(9): 2965-77.

Murphy, W. J., K. P. Watkins, et al. (1986). "Identification of a novel Y branch structure as an intermediate in trypanosome mRNA processing: evidence for trans splicing." *Cell* 47(4): 517-25.

Nelson, D. W. and B. M. Honda (1989). "Two highly conserved transcribed regions in the 5S DNA repeats of the nematodes *Caenorhabditis elegans* and *Caenorhabditis briggsae*."*Nucleic Acids Res* 17(21): 8657-67.

Nilsen, T. W. (2001). "Evolutionary origin of SL-addition trans-splicing: still an enigma." *Trends Genet* 17(12): 678-80.

Rajkovic, A., R. E. Davis, et al. (1990). "A spliced leader is present on a subset of mRNAs from the human parasite Schistosoma mansoni." *Proc Natl Acad Sci USA* 87(22): 8879-83.

Reinke, V. (2002). "Functional exploration of the *C. elegans* genome using DNA microarrays." *Nat Genet* 32 Suppl: 541-6.

Riddle, D. L., T. Blumenthal, et al., Eds. (1997). *C. Elegans II*. Plainfield, N.Y., Cold Spring Harbor Press.

Ross, L. H., J. H. Freedman, et al. (1995). "Structure and expression of novel spliced leader RNA genes in *Caenorhabditis elegans*." *J Biol Chem* 270(37): 22066-75.

Roy, P. J., J. M. Stuart, et al. (2002). "Chromosomal clustering of muscle-expressed genes in *Caenorhabditis elegans*." *Nature* 418(6901): 975-9.

Sambrook, J. and D. W. Russell (2001). *Molecular cloning: a laboratory manual*. Cold Spring Harbor, N.Y., Cold Spring Harbor Laboratory Press.

Scharfmann, R., J. H. Axelrod, et al. (1991). "Long-term in vivo expression of retrovirus-mediated gene transfer in mouse fibroblast implants." *Proc Natl Acad Sci USA* 88(11): 4626-30.

Sharp, P. A. (1987). "Trans splicing: variation on a familiar theme?" *Cell* 50(2): 147-8.

Solnick, D. (1985). "Trans splicing of mRNA precursors." *Cell* 42(1): 157-64.

Stinchcomb, D. T., J. E. Shaw, et al. (1985). "Extrachromosomal DNA transformation of Caenorhabditis elegans." *Mol Cell Biol* 5(12): 3484-96.

Stover, N. A. and R. E. Steele (2001). "Trans-spliced leader addition to mRNAs in a cnidarian." *Proc Natl Acad Sci USA* 98(10): 5693-8.

Sturm, N. R., J. Fleischmann, et al. (1998). "Efficient trans-splicing of mutated spliced leader exons in Leishmania tarentolae." *J Biol Chem* 273(30): 18689-92.

Sturrock, R. R. (1988). "The beta astrocyte: its possible role as a central nervous system phagocyte." *Anat Anz* 166(1-5): 331-40.

Sutton, R. E. and J. C. Boothroyd (1986). "Evidence for trans splicing in trypanosomes." *Cell* 47(4): 527-35.

Sutton, R. E. and J. C. Boothroyd (1988). "Trypanosome trans-splicing utilizes 2'-5' branches and a corresponding debranching activity." *Embo J* 7(5): 1431-7.

Takacs, A. M., J. A. Denker, et al. (1988). "A 22-nucleotide spliced leader sequence in the human parasitic nematode Brugia malayi is identical to the trans-spliced leader exon in *Caenorhabditis elegans*." *Proc Natl Acad Sci USA* 85(21): 7932-6.

Takeda, J., H. Yano, et al. (1993). "A molecular inventory of human pancreatic islets: sequence analysis of 1000 cDNA clones." *Hum Mol Genet* 2(11): 1793-8.

Tessier, L. H., M. Keller, et al. (1991). "Short leader sequences may be transferred from small RNAs to premature mRNAs by trans-splicing in Euglena." *Embo J* 10(9): 2621-5.

Thomas, J. D., R. C. Conrad, et al. (1988). "The *C. elegans* trans-spliced leader RNA is bound to Sm and has a trimethylguanosine cap." *Cell* 54(4): 533-9.

U.S. Pat. No. 4,736,866.

U.S. Pat. No. 5,162,215.

U.S. Pat. No. 5,489,742.
U.S. Pat. No. 5,550,316.
U.S. Pat. No. 5,573,933.
U.S. Pat. No. 5,614,396.
U.S. Pat. No. 5,648,061.
U.S. Pat. No. 5,741,957.
Van Doren, K. and D. Hirsh (1988). "Trans-spliced leader RNA exists as small nuclear ribonucleoprotein particles in Caenorhabditis elegans." *Nature* 335(6190): 556-9.
Vandenberghe, A. E., T. H. Meedel, et al. (2001). "mRNA 5'-leader trans-splicing in the chordates." *Genes Dev* 15(3): 294-303.
Way, J. C. and M. Chalfie (1989). "The mec-3 gene of *Caenorhabditis elegans* requires its own product for maintained expression and is expressed in three neuronal cell types." *Genes Dev* 3(12A): 1823-33.
White, J. G. (1986). "The structure of the nervous system of the nematode *C. elegans.*" *Philos. Trans. R. Soc. Lond. B. Biol. Sci.* 314:1-340.
White, O., T. Dunning, et al. (1993). "A quality control algorithm for DNA sequencing projects." *Nucleic Acids Res* 21(16): 3829-38.
Williams, P. L. and D. B. Dusenbery (1990). "Aquatic toxicity testing using the nematode *Caenorhabditis elegans.*" *Environmental Toxicology and Chemistry* 9: 1285-1290.
Williams, R. S., J. A. Thomas, et al. (1993). "Human heat shock protein 70 (hsp70) protects murine cells from injury during metabolic stress." *J Clin Invest* 92(1): 503-8.
Xie, H. and D. Hirsh (1998). "In vivo function of mutated spliced leader RNAs in *Caenorhabditis elegans.*" *Proc Natl Acad Sci USA* 95(8): 4235-40.
Zeng, W. and J. E. Donelson (1992). "The actin genes of Onchocerca volvulus." *Mol Biochem Parasitol* 55(1-2): 207-16.
Zhang, Y., C. Ma, et al. (2002). "Identification of genes expressed in *C. elegans* touch receptor neurons." *Nature* 418(6895): 331-5.
Zorio, D. A., N. N. Cheng, et al. (1994). "Operons as a common form of chromosomal organization in *C. elegans.*" *Nature* 372(6503): 270-2.

It will be understood that various details of the described subject matter can be changed without departing from the scope of the described subject matter. Furthermore, the foregoing description is for the purpose of illustration only, and not for the purpose of limitation.

What is claimed is:

1. A method for isolating a trans-spliced ribonucleic acid molecule from a cell, the method comprising:
   (a) introducing into the cell a nucleic acid molecule encoding a derivatized spliced leader RNA (SLRNA) molecule, wherein the derivatized SLRNA molecule comprises a spliced leader (SL) mini-exon sequence comprising a unique sequence;
   (b) expressing the derivatized SLRNA in the cell, wherein the expressing results in the spliced leader sequence being trans-spliced onto a ribonucleic acid molecule; and
   (c) isolating the trans-spliced ribonucleic acid molecule comprising the spliced leader sequence.

2. The method of claim 1, further comprising sequencing the trans-spliced ribonucleic acid molecule or a reverse transcription product thereof.

3. A method for identifying a plurality of ribonucleic acid molecules expressed in a cell, the method comprising:
   (a) introducing into the cell a derivatized spliced leader RNA (SLRNA) molecule, wherein the derivatized SLRNA molecule comprises a spliced leader (SL) mini-exon sequence comprising a unique sequence;
   (b) expressing the derivatized SLRNA in the cell, wherein the expressing results in the spliced leader sequence being trans-spliced onto a ribonucleic acid molecule; and
   (c) isolating the trans-spliced ribonucleic acid molecule comprising the spliced leader sequence.

4. The method of claim 3, further comprising sequencing at least one of the plurality of trans-spliced ribonucleic acid molecules or a reverse transcription product thereof.

5. The method of claim 3, further comprising creating a library comprising the plurality of trans-spliced ribonucleic acid molecules.

6. The method of one of claims 1 and 3, wherein the cell is present in an organism.

7. The method of claim 6, wherein the organism is selected from the group consisting of cnidarians, ascidians, nematodes, trematodes, cestodes, helminthes, avians, and mammals.

8. The method of claim 7, wherein the organism is selected from the group consisting of *C. elegans, Schistosoma* sp., soil-transmitted helminthes, *Onchocerca volvulus, Brugia malayi, Heterorhabditis bacteriophora, Haemonchus contortus,* and *Wucheria bancrofti.*

9. The method of one of claims 1 and 3, wherein the introducing is accomplished by introducing into the cell a nucleic acid encoding a transgenic SLRNA molecule, wherein the transgenic SLRNA molecule comprises a spliced leader sequence comprising a unique sequence.

10. The method of one of claims 1 and 3, further comprising mutagenizing an endogenous SLRNA gene to a non-functional form.

11. A method for detectably labeling a ribonucleic acid present in a cell of interest, the method comprising introducing into the cell a nucleic acid molecule comprising a nucleotide sequence encoding a 5' spliced leader (SL) sequence comprising a detectable label, wherein the nucleotide sequence encoding the 5' SL sequence is operably linked to a promoter capable of directing transcription of the 5' SL sequence in the cell of interest, and further wherein the cell of interest is present in an organism.

12. The method of claim 11, wherein the organism is selected from the group consisting of cnidarians, ascidians, nematodes, trematodes, cestodes, helminthes, avians, and mammals.

13. The method of claim 11, wherein the organism is selected from the group consisting of *C. elegans, Schistosoma* sp., soil-transmitted helminthes, *Onchocerca volvulus, Brugia malayl, Heterorhabditis bactedophora, Haemonchus contortus,* and *Wucheria bancroffi.*

14. The method of claim 12, wherein the cell of interest is selected from the group consisting of an endothelial cell, a gonadal cell, a gut cell, neuronal cells, endothelial cells, gonadal cells, gut cells, muscle cells, duct cells, sheath cells, pharyngeal cells, vulval cells, ray cells, labial cells, excretory cells, sperm, oocytes, and coelomocytes.

15. The method of claim 14, wherein the neuronal cells are selected from the group consisting of motor neurons, sensory neurons, interneurons, ring neurons, serotonergic neurons, glutamatergic neurons, GABAergic neurons, dopaminergic neurons, and cholinergic neurons.

16. The method of claim 15, wherein the sensory neurons are selected from the group consisting of including mechanosensory, thermosensory and chemosensory neurons.

17. A method for isolating a gene affecting a phenotype of interest, the method comprising:

(a) introducing into a cell expressing a phenotype of interest one or more trans-spliced ribonucleic acid molecules, wherein the one or more trans-spliced ribonucleic acid molecules are expressed in a cell, tissue, organ, or organism of predetermined phenotype;

(b) identifying a cell and/or organism with an altered and/or desired phenotype; and (c) isolating a trans-spliced ribonucleic acid molecule effecting said altered and/or desired phenotype.

18. The method of claim 17, further comprising creating a library comprising the plurality of the one or more of the trans-spliced ribonucleic acid molecules.

19. The method of claim 17, wherein the phenotype of interest is altered to a native and/or 'wild-type' phenotype.

20. The method of claim 17, further comprising sequencing the trans-spliced ribonucleic acid molecule effecting the altered and/or desired phenotype.

21. The method of claim 17, wherein one, more than one, or a plurality of trans-spliced ribonucleic acid molecules are operably linked to a promoter capable of directing transcription of said trans-spliced ribonucleic acid molecules in a cell and/or tissue and/or organ and/or organism of interest.

22. The method of claim 17, further comprising isolating said trans-spliced ribonucleic acid molecule effecting said altered and/or desired phenotype via the Polymerase Chain Reaction.

23. The method of claim 17, further comprising truncating said trans-spliced ribonucleic acid molecule by use of a Class II and or Class IIS restriction endonuclease, wherein truncation removes all or portions of the trans-spliced leader sequence.

* * * * *